US012687540B2

(12) United States Patent
Pham et al.

(10) Patent No.: US 12,687,540 B2
(45) Date of Patent: Jul. 21, 2026

(54) AMYLOID-BINDING COMPOUNDS AND METHODS OF USE THEREOF

(71) Applicant: Vanderbilt University, Nashville, TN (US)

(72) Inventors: Wellington Pham, Nashville, TN (US); Richard A. McClure, Nashville, TN (US); William James Behof, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 697 days.

(21) Appl. No.: 16/925,105

(22) Filed: Jul. 9, 2020

(65) Prior Publication Data

US 2021/0011008 A1 Jan. 14, 2021

Related U.S. Application Data

(60) Provisional application No. 62/872,190, filed on Jul. 9, 2019.

(51) Int. Cl.
*G01N 33/542* (2006.01)
*A61K 49/14* (2006.01)

(52) U.S. Cl.
CPC ........... *G01N 33/542* (2013.01); *A61K 49/14* (2013.01); *G01N 2333/4709* (2013.01); *G01N 2458/00* (2013.01); *G01N 2458/15* (2013.01)

(58) Field of Classification Search
CPC .... A61K 51/00; A61K 51/04; A61K 51/0465; A61K 49/00; A61K 49/14; G01N 33/542; G01N 2333/4709; G01N 2458/00; G01N 2458/15
USPC .......... 424/1.11, 1.65, 1.69, 1.73, 1.81, 1.89, 424/9.1, 9.2, 9.4
See application file for complete search history.

(56) References Cited

U.S. PATENT DOCUMENTS

2006/0275209 A1* 12/2006 Schweiger .............. C07B 59/00 544/37

FOREIGN PATENT DOCUMENTS

EP 1667947 B1 * 8/2008 ............. C07B 59/00

OTHER PUBLICATIONS

McClure et al (Neuroimage Clinical, vol. 2, pp. 620-629) (Year: 2013).*
Yeung et al, Journal of Chromatography, vol. 303, pp. 412-416 (Year: 1984).*
Weuve, J., Hebert, L. E., Scherr, P. A., and Evans, D. A. (2014) Deaths in the United States among persons with Alzheimer's disease (2010-2050). Alzheimers Dement 10, e40-46.
Philibert, K. D., Marr, R. A., Norstrom, E. M., and Glucksman, M. J. (2014) Identification and characterization of Abeta peptide interactors in Alzheimer's disease by structural approaches. Front Aging Neurosci 6, 265.
Macias, M. P., Gonzales, A. M., Siniard, A. L., Walker, A. W., Corneveaux, J. J., Huentelman, M. J., Sabbagh, M. N., and Decourt, B. (2014) A cellular model of amyloid precursor protein processing and amyloid-beta peptide production. J Neurosci Methods 223, 114-122.
Selkoe, D. J. (2011) Alzheimer's disease. Cold Spring Harb Perspect Biol 3, 1-16.
Weller, R. O., Subash, M., Preston, S. D., Mazanti, I., and Carare, R. O. (2008) Perivascular drainage of amyloid-beta peptides from the brain and its failure in cerebral amyloid angiopathy and Alzheimer's disease. Brain Pathol 18, 253-266.
Viola, K. L., and Klein, W. L. (2015) Amyloid beta oligomers in Alzheimer's disease pathogenesis, treatment, and diagnosis. Acta Neuropathol 129, 183-206.
Ryan, T. M., Roberts, B. R., McColl, G., Hare, D. J., Doble, P. A., Li, Q. X., Lind, M., Roberts, A. M., Mertens, H. D., Kirby, N., Pham, C. L., Hinds, M. G., Adlard, P. A., Barham, K. J., Curtain, C. C., and Masters, C. L. (2015) Stabilization of nontoxic Abeta-oligomers: insights into the mechanism of action of hydroxyquinolines in Alzheimer's disease. J Neurosci 35, 2871-2884.
Matsuzaki, K. (2014) How do membranes initiate Alzheimer's disease? formation of toxic amyloid fibrils by the amyloid beta-protein ganglioside clusters. Acc Chem Res 47, 2397-of 2404.
Hong, S., Ostaszewski, B. L., Yang, T., O'Malley, T. T., Jin, M., Yanagisawa, K., Li, S., Bartels, T., and Selkoe, D. J. (2014) Soluble Abeta oligomers are rapidly sequestered from brain ISF in vivo and bind GM1 ganglioside on cellular membranes. Neuron 82, 308-319.
Collins-Praino, L. E., Francis, Y. I., Griffith, E. Y., Wiegman, A. F., Urbach, J., Lawton, A., Honig, L. S., Cortes, E., Vonsattel, J. P., Canoll, P. D., Goldman, J. E., and Brickman, A. M. (2014) Soluble amyloid beta levels are elevated in the white matter of Alzheimer's patients, independent of cortical plaque severity. Acta Neuropathol Commun 2, 83.
Chen, J., Armstrong, A. H., Koehler, A. N., and Hecht, M. H. (2010) Small molecule microarrays enable the discovery of compounds that bind the Alzheimer's Abeta peptide and reduce its cytotoxicity. J Am Chem Soc 132, 17015-17022.

(Continued)

*Primary Examiner* — D. L. Jones
(74) *Attorney, Agent, or Firm* — Stites & Harbison PLLC; Richard S. Myers, Jr.

(57) ABSTRACT

A method of screening for amyloid-binding compounds, amyloid-binding compounds, and a method of detecting amyloid-β (Abeta) plaques in a subject are disclosed. The method of screening for amyloid-binding compounds includes combining amyloid, a dye, and at least one test compound to form a sample solution; equilibrating the sample solution; measuring a fluorescence signal of the sample solution; and comparing the measured fluorescence signal of the sample to a control; wherein attenuation of the fluorescence signal, as compared to the control, indicates that one or more of the test compounds bind amyloid. The amyloid-binding compound includes a compound detected by the screening method. The method of detecting amyloid-β (Abeta) plaques in a subject includes administering one or more of the amyloid-binding compounds to the subject, and detecting the compound within the subject.

6 Claims, 8 Drawing Sheets

Specification includes a Sequence Listing.

(56) References Cited

OTHER PUBLICATIONS

Inglese, J., Shamu, C. E., and Guy, R. K. (2007) Reporting data from high-throughput screening of small-molecule libraries. Nat Chem Biol 3, 438-441.
Nolting, D. D., Gore, J. C., and Pham, W. (2011) Near-Infrared Dyes: Probe Development and Applications in Optical Molecular Imaging. Annual review of cell and developmental biology 8, 521-534.
Nesterov, E. E., Skoch, J., Hyman, B. T., Klunk, W. E., Bacskai, B. J., and Swager, T. M. (2005) In vivo optical imaging of amyloid aggregates in brain: design of fluorescent markers. Angewandte Chemie (International ed 44, 5452-5456.
Hudson, S. A., Ecroyd, H., Kee, T. W., and Carver, J. A. (2009) The thioflavin T fluorescence assay for amyloid fibril detection can be biased by the presence of exogenous compounds. FEBS J 276, 5960-5972.
Khurana, R., Coleman, C., Ionescu-Zanetti, C., Carter, S. A., Krishna, V., Grover, R. K., Roy, R., and Singh, S. (2005) Mechanism of thioflavin T binding to amyloid fibrils. J Struct Biol 151, 229-238.
LeVine III, H. (1993) Thioflavine T interaction with synthetic Alzheimer's diease beta-amyloid peptides: detection of amyloid aggregation in solution. Protein Sci 2, 404-410.
Naiki, H., Higuchi, K., Hosokawa, M., and Takeda, T. (1989) Fluorometric determination of amyloid fibrils in vitro using the fluorescent dye, thioflavin T1. Anal Biochem 177, 244-249.
Klunk, W. E., Jacob, R. F., and Mason, R. P. (1999) Quantifying amyloid by congo red spectral shift assay. Methods Enzymol 309, 285-305.
Klunk, W. E., Jacob, R. F., and Mason, R. P. (1999) Quantifying amyloid beta-peptide (Abeta) aggregation using the Congo red-Abeta (CR-abeta) spectrophotometric assay. Anal Biochem 266, 66-76.
Nakagami, Y., Nishimura, S., Murasugi, T., Kubo, T., Kaneko, I., Meguro, M., Marumoto, S., Kogen, H., Koyama, K., and Oda, T. (2002) A novel compound RS-0466 reverses beta-amyloid-induced cytotoxicity through the Akt signaling pathway in vitro. Eur J Pharmacol 457, 11-17.
Nishimura, S., Murasugi, T., Kubo, T., Kaneko, I., Meguro, M., Marumoto, S., Kogen, H., Koyama, K., Oda, T., and Nakagami, Y. (2003) RS-4252 inhibits amyloid beta-induced cytotoxicity in HeLa cells. Pharmacol Toxicol 93, 29-32.
Wood, S. J., Mackenzie, L., Maleeff, B., Hurle, M. R., and Wetzel, R. (1996) Selective inhibition of Abeta fibril formation. J Biol Chem 271, 4086-4092.
Manzoni, C., Colombo, L., Messa, M., Cagnotto, A., Cantu, L., Del Favero, E., and Salmona, M. (2009) Overcoming synthetic Abeta peptide aging: a new approach to an age-old problem. Amyloid 16, 71-80.
Oakley, H., Cole, S. L., Logan, S., Maus, E., Shao, P., Craft, J., Guillozet-Bongaarts, A., Ohno, M., Disterhoft, J., Van Eldik, L., Berry, R., and Vassar, R. (2006) Intraneuronal beta-amyloid aggregates, neurodegeneration, and neuron loss in transgenic mice with five familial Alzheimer's disease mutations: potential factors in amyloid plaque formation. J Neurosci 26, 10129-10140.
Selkoe, D. J., and Hardy, J. (2016) The amyloid hypothesis of Alzheimer's disease at 25 years. EMBO Mol Med 8, 595-608.
Parikh, N. D., and Klimov, D. K. (2015) Molecular Mechanisms of Alzheimer's Biomarker FDDNP Binding to Abeta Amyloid Fibril. J Phys Chem B 119, 11568-11580.
He, H., Xu, J., Cheng, D. Y., Fu, L., Ge, Y. S., Jiang, F. L., and Liu, Y. (2017) Identification of Binding Modes for Amino Naphthalene 2-Cyanoacrylate (ANCA) Probes to Amyloid Fibrils from Molecular Dynamics Simulations. J Phys Chem B 121, 1211-1221.
Klunk, W. E., Wang, Y., Huang, G. F., Debnath, M. L., Holt, D. P., Shao, L., Hamilton, R. L., Ikonomovic, M. D., DeKosky, S. T., and Mathis, C. A. (2003) The binding of 2-(4'-methylaminophenyl)benzothiazole to postmortem brain homogenates is dominated by the amyloid component. J Neurosci 23, 2086-2092.
Doig, A. J., Del Castillo-Frias, M. P., Berthoumieu, O., Tarus, B., Nasica-Labouze, J., Sterpone, F., Nguyen, P. H., Hooper, N. M., Faller, P., and Derreumaux, P. (2017) Why Is Research on Amyloid-beta Failing to Give New Drugs for Alzheimer's Disease? ACS Chem Neurosci 8, 1435-1437.
Jerabek, J., Uliassi, E., Guidotti, L., Korabecny, J., Soukup, O., Sepsova, V., Hrabinova, M., Kuca, K., Bartolini, M., Pena-Altamira, L. E., Petralla, S., Monti, B., Roberti, M., and Bolognesi, M. L. (2017) Tacrine-resveratrol fused hybrids as multi-target-directed ligands against Alzheimer's disease. Eur J Med Chem 127, 250-262.
Loureiro, J. A., Andrade, S., Duarte, A., Neves, A. R., Queiroz, J. F., Nunes, C., Sevin, E., Fenart, L., Gosselet, F., Coelho, M. A., and Pereira, M. C. (2017) Resveratrol and Grape Extract-loaded Solid Lipid Nanoparticles for the Treatment of Alzheimer's Disease. Molecules 22.
Moussa, C., Hebron, M., Huang, X., Ahn, J., Rissman, R. A., Aisen, P. S., and Turner, R. S. (2017) Resveratrol regulates neuro-inflammation and induces adaptive immunity in Alzheimer's disease. J Neuroinflammation 14, 1.
Sarubbo, F., Moranta, D., Asensio, V. J., Miralles, A., and Esteban, S. (2017) Effects of Resveratrol and other Polyphenols on the most common Brain Age-Related Diseases. Curr Med Chem.
McClure, R. A., Chumbley, C. W., Reyzer, M. L., Wilson, K., Caprioli, R. M., Gore, J. C., and Pham, W. (2013) Identification of promethazine as an amyloid-binding molecule using a fluorescence high-throughput assay and MALDI imaging mass spectrometry. NeuroImage:Clinical 2, 620-629.
Day, L. R., gGbson, W., and Williams, K. P. (2010) Development of a high throughput screening assay for inhibitors of hedgehog-heparin interactions. int J High Throughput Screening 1, 69-80.

* cited by examiner

| | Positive control (5XFAD brain lysate) | Negative control (wt brain lysate) | Percent coefficient of variation |
|---|---|---|---|
| Average | 2098.73 | 1069.44 | 0.04 |
| Standard deviation | 85.02 | 46.68 | 0.04 |
| Z'-factor | | | > 0.6215 |

AMYLOID-BINDING COMPOUNDS AND METHODS OF USE THEREOF

RELATED APPLICATIONS

This application claims the benefit of U.S. Provisional Application Ser. No. 62/872,190, filed Jul. 9, 2019, the entire disclosure of which is incorporated herein by this reference.

GOVERNMENT INTEREST

This invention was made with government support under Grant no. AG061138, awarded by the National Institutes of Health. The government has certain rights to this invention.

SEQUENCE LISTING

The instant application contains a Sequence Listing which has been submitted in ASCII format via EFS-Web and is hereby incorporated by reference in its entirety. The ASCII copy of the Sequence Listing, which was created on Jul. 9, 2020, is named 11672N-19163U.txt and is 1.33 kilobytes in size.

TECHNICAL FIELD

The present invention relates to amyloid-binding compounds and methods of use thereof. In particular, the presently-disclosed subject matter relates to compounds that bind amyloid-β (Abeta) plaques, methods of screening to identify these compounds, and the conversion into positron emission tomography (PET) probes for noninvasive in vivo imaging applications of these compounds.

BACKGROUND

With the prevalence of Alzheimer's disease (AD) projected to rise dramatically in the coming decades, there is an increasing urgency to develop novel therapies for the prevention and treatment of this debilitating disease. Currently, the mechanism that regulates neuronal degeneration in AD remains unknown; however, the cytopathological hallmarks of AD appear to be the formation of amyloid-β (Abeta) plaques between the neurons, which leads ultimately to profound neuron toxicity and atrophy. According to the Abeta cascade hypothesis, failure to eliminate soluble Abeta from the brain results in Abeta aggregation, which alters homeostasis and neuronal environment resulting in cognitive decline and dementia. Therefore, if Abeta plaques are an underlying mechanism that causes dementia, preventing their formation or dismantling existing plaques, specifically at the early onset of the disease, would be an ultimate goal to prevent AD.

Given the critical unmet medical needs in AD, there has been considerable interest in the identification of novel Abeta binding/inhibitor molecules. Rational design of Abeta inhibitors is hampered due to the lack of high-resolution structures of Abeta plaques. A large number of reports in the literature describe a range of intermediates along the Abeta aggregation pathway that have been implicated as potentially toxic species. However, at present no detailed structural information is available for Abeta fibrils, as knowing which parts of Abeta are important for filament formation is relevant for the development of drugs, owing to their short-lived intermediates and their insoluble nature. As a result, there is still enormous uncertainty over the question whether rationally structural-based drug design of Abeta inhibitors is an effective approach to identify Abeta-binding inhibitors.

One of the alternative approaches focuses on high throughput screening (HTS). In fact, the flexibility of HTS has allowed numerous and disparate areas of biology to engage with an equally diverse palate of chemistry. For example, some HTS assays utilize fluorescence (FL) dyes, such as thioflavin-T, which exhibits increased FL when bound to a target. This dynamic reporter has been exploited to monitor fibrillary kinetics in real time, and produced single time-point readouts. LeVine et al. first reported the use of this technique for screening Abeta-binding compounds. Klunk et al. employed this dynamic reporter to develop quantitative methods to determine the properties of Abeta peptide aggregation. Since then, a number of high-throughput methods have been derived to screen for compounds able to interfere with Abeta aggregation.

To date, all of the screening assays discussed above have been limited to screening a small number of molecules, and many, if not all, still employed synthetic Abeta peptides as a surrogate for endogenous Abeta in the brain during the assay. The rationale for this approach is the ease of using synthetic peptides, which can be stored as lyophilized powders and the process of amyloidogenesis can be achieved by simply dissolving the peptides in conditioned buffers. Simple as this system seems, it is nevertheless often influenced by the tendency of different batches of peptides to vary in their secondary structure and aggregation state. The formation of plaques using peptides is a complex process, which is based on a continuous process involving protein misfolding, association and conformational rearrangements, and all depend on time, solvents and handling procedures. As a result, this error-prone process has a proclivity for inconsistent outcomes, and hit compounds identified from such operations do not always have the same effect in vivo.

Accordingly, there remains a need for a reliable and reproducible assay.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

In some embodiments, the presently-disclosed subject matter includes a method of screening for amyloid-binding compounds, the method comprising combining amyloid, a dye, and at least one test compound to form a sample solution; equilibrating the sample solution; measuring a fluorescence signal of the sample solution; and comparing the measured fluorescence signal of the sample to a control; wherein attenuation of the fluorescence signal, as compared to the control, indicates that one or more of the test compounds bind amyloid. In some embodiments, the amyloid is endogenous amyloid. In one embodiment, the endogenous amyloid is provided in brain lysate. In some embodiments, the amyloid is amyloid-β (Abeta). In one embodiment, the Abeta includes Abeta plaques. In some embodiments, the larger the decrease in fluorescence the stronger the binding of the test compound. In some embodiments, the test compound is selected from a group of compounds capable of penetrating the blood-brain barrier (BBB). In one embodiment, the group of compounds capable of penetrating the BBB consist of compounds having suitable log P values. In some embodiments, the dye is selected from the group consisting of Thioflavin-T, Thioflavin-S, and Congo red.

Also provided herein, in some embodiments, is an amyloid-binding compound comprising a compound detected by the method disclosed herein. In some embodiments, the compound includes a phenothiazine ring. In one embodiment, the compound include promethazine or a promethazine analog. In another embodiment, the promethazine analog is selected from the group consisting of:

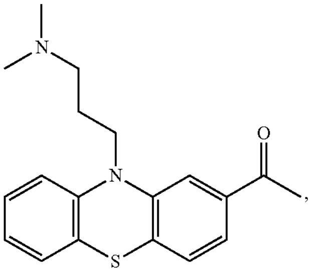

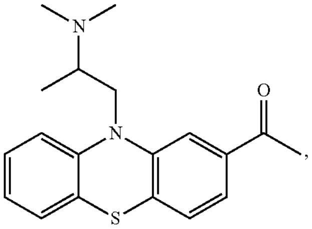

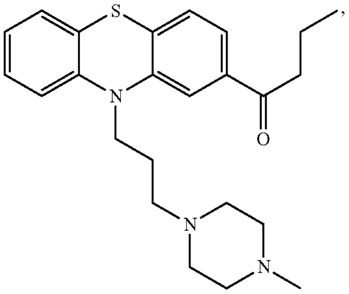

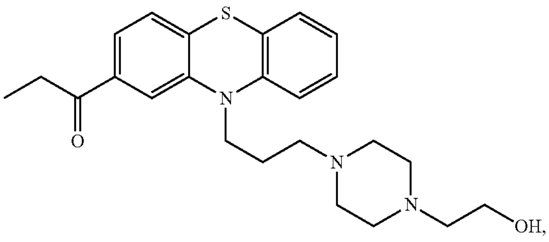

-continued

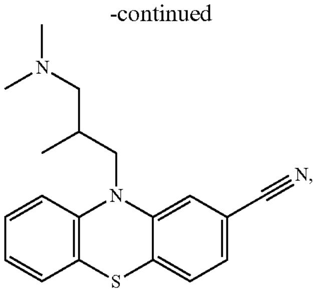

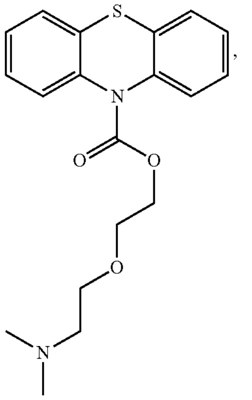

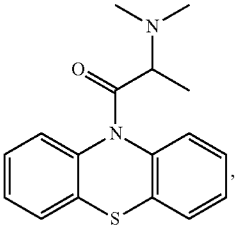

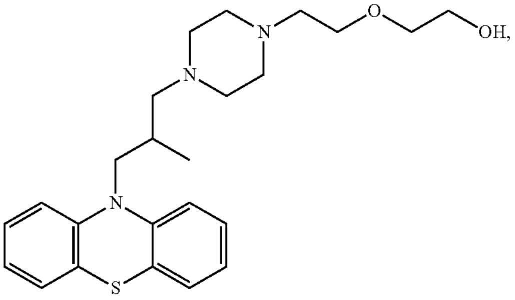

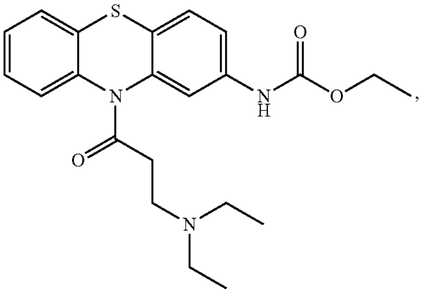

-continued
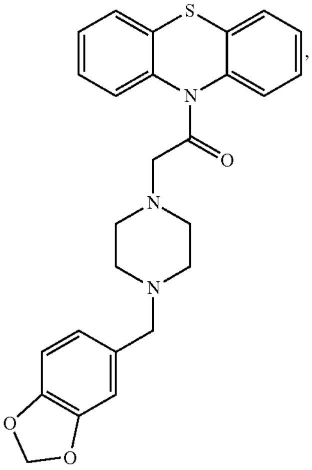
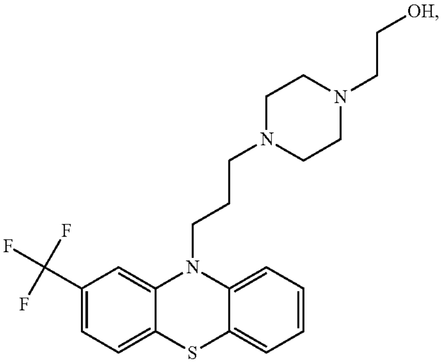
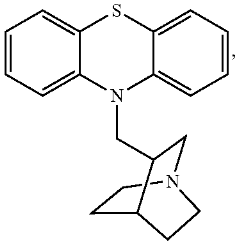
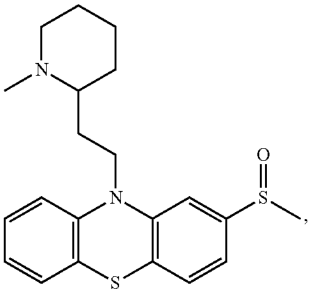
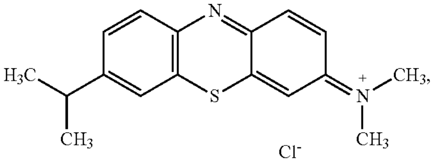
-continued
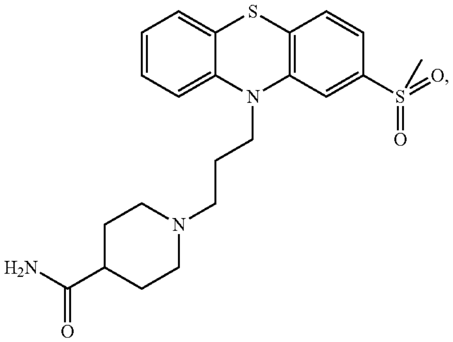
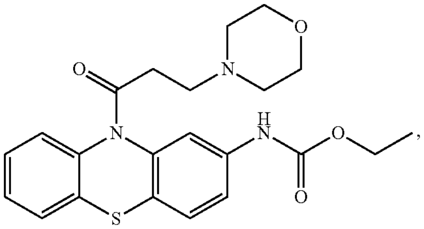
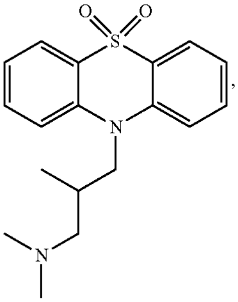
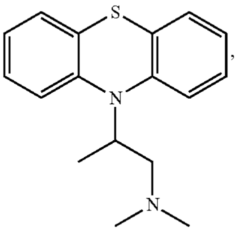
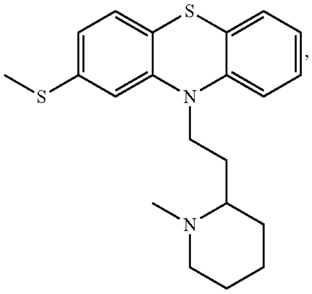
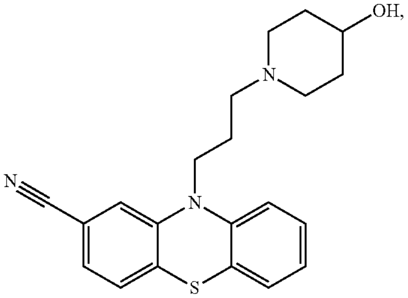

-continued

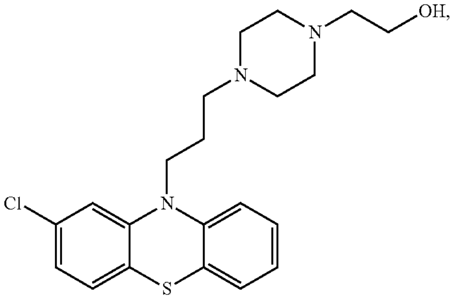

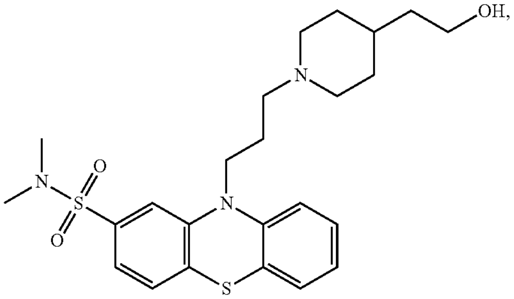

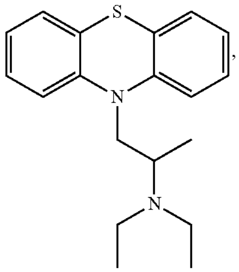

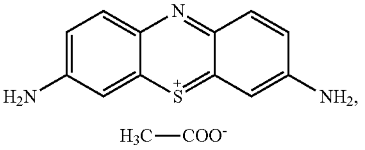

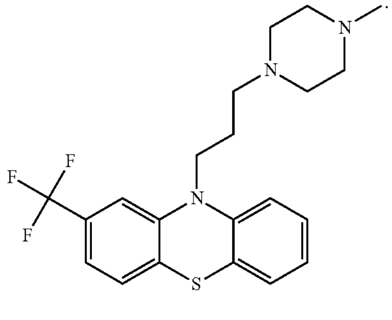

-continued

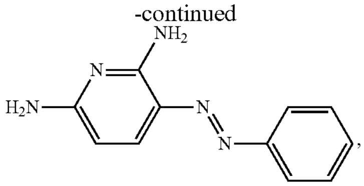

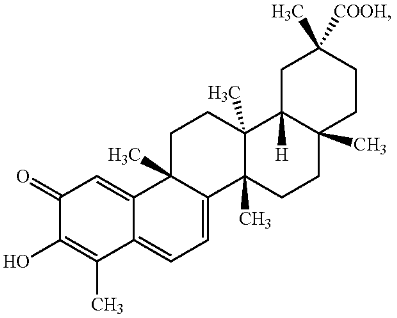

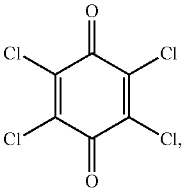

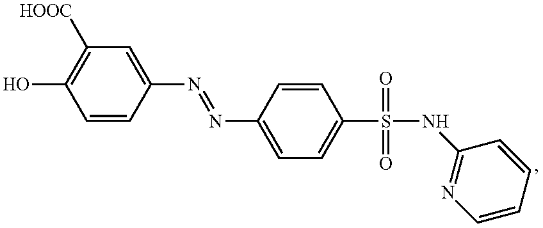

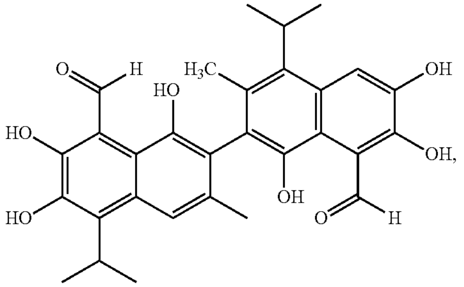

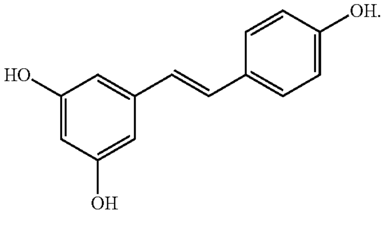

In some embodiments, the compound is selected from the group consisting of:

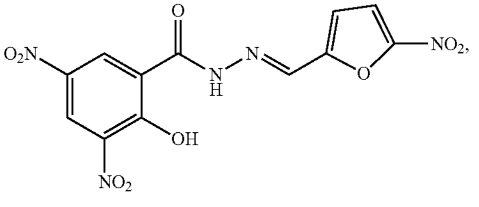

In some embodiments, the compound further comprises a positron emission tomography (PET) label. In one embodiment, the PET label is an isotope. In another embodiment, the isotope is [$^{11}$C]carbon, [$^{18}$F]fluoride, [$^{68}$Ga]gallium, or [$^{64}$Cu]copper. In a further embodiment, the isotope is [$^{11}$C] carbon.

A method of detecting amyloid-β (Abeta) plaques in a subject, the method including administering one or more of the compounds disclosed herein to the subject; and detecting the compound within the subject. In some embodiments, the one or more compounds are isotope-labeled and the detection is through autoradiography.

Further features and advantages of the presently-disclosed subject matter will become evident to those of ordinary skill in the art after a study of the description, figures, and non-limiting examples in this document.

BRIEF DESCRIPTION OF THE DRAWINGS

The presently-disclosed subject matter will be better understood, and features, aspects and advantages other than those set forth above will become apparent when consideration is given to the following detailed description thereof. Such detailed description makes reference to the following drawings, wherein.

Figure 1A:
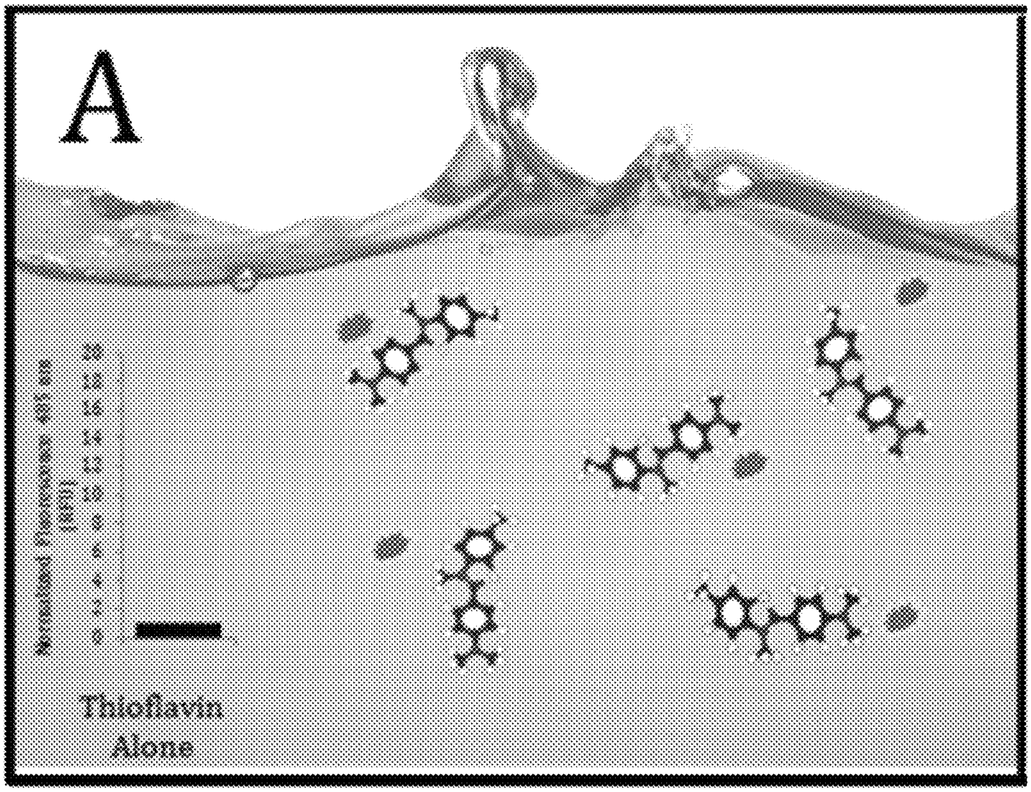
FIGS. 1A-C show images illustrating topologically activated property of Thioflavin-T. (A) Insignificant FL signal in free solution. (B) Enhanced FL signal upon binding to Abeta plaques from 5XFAD brain lysate. (C) An inhibitor competes with Thioflavin-T for Abeta resulted in reduced FL signal.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims, unless the context clearly dictates otherwise. Thus, for example, reference to "a polypeptide" includes one or more of such polypeptides, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Provided herein, in some embodiments, are methods of screening for amyloid-binding compounds. In some embodiments, the method of screening for amyloid-binding compounds includes using a novel high-throughput screening (HTS) assay. For example, in some embodiments, the HTS assay is a high-throughput amyloid Thioflavin competitive binding optical assay (HATCO) to identify Abeta-binding molecules. In some embodiments, the HATCO assay relies on the fluorescence (FL) readout of Thioflavin-T. According to the quantum mechanics theory, this class of FL dyes possesses substantial conformational freedom while remaining in free solution, and thus rapidly quenches excited states generated by photon excitation and exhibits a relatively low FL signal. However, upon binding to Abeta plaques, the conformation freedom is dramatically reduced. This increased structural rigidity decreases the vibrational and rotational processes, which results in a decreased radiation decay rate in both ground and excited states. Cumulatively, this phenomenon contributes to an observed increase in the FL quantum yield when bound to Abeta plaques as compared to the unbound state. Although discussed herein primarily with respect to Thioflavin-T, as will be understood by those skilled in the art, the disclosure is not so limited and includes other suitable dyes such as, but not limited to, Thioflavin-S or Congo Red.

Figure 1B:
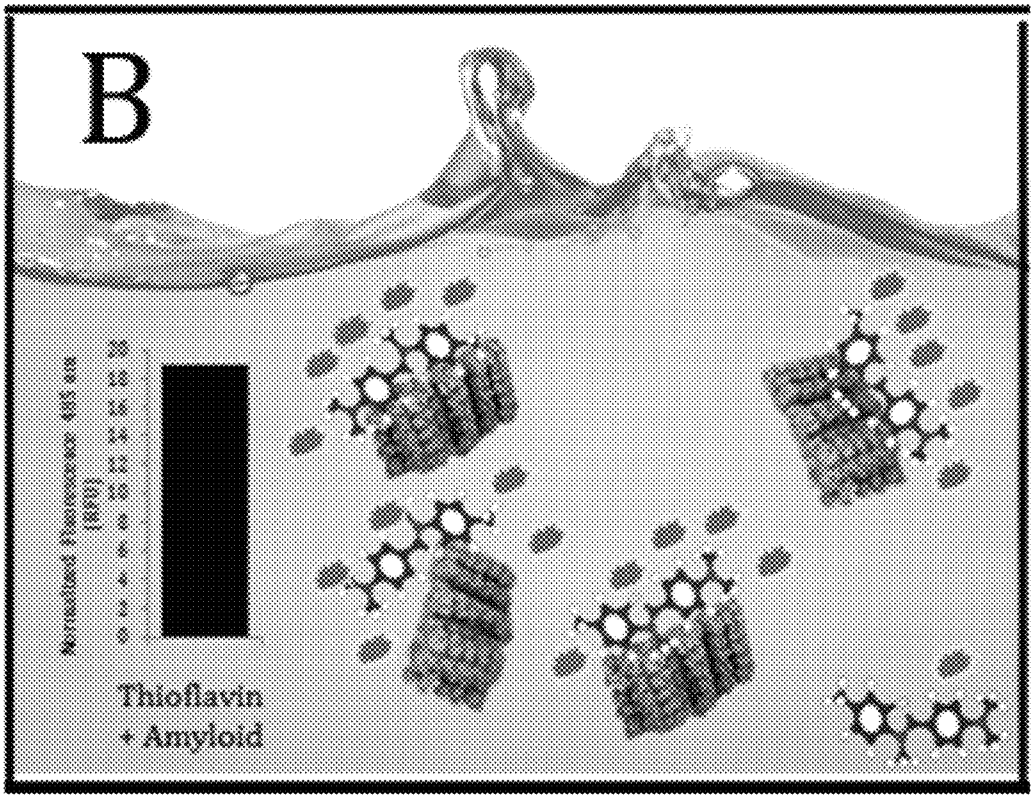
Figure 1C:
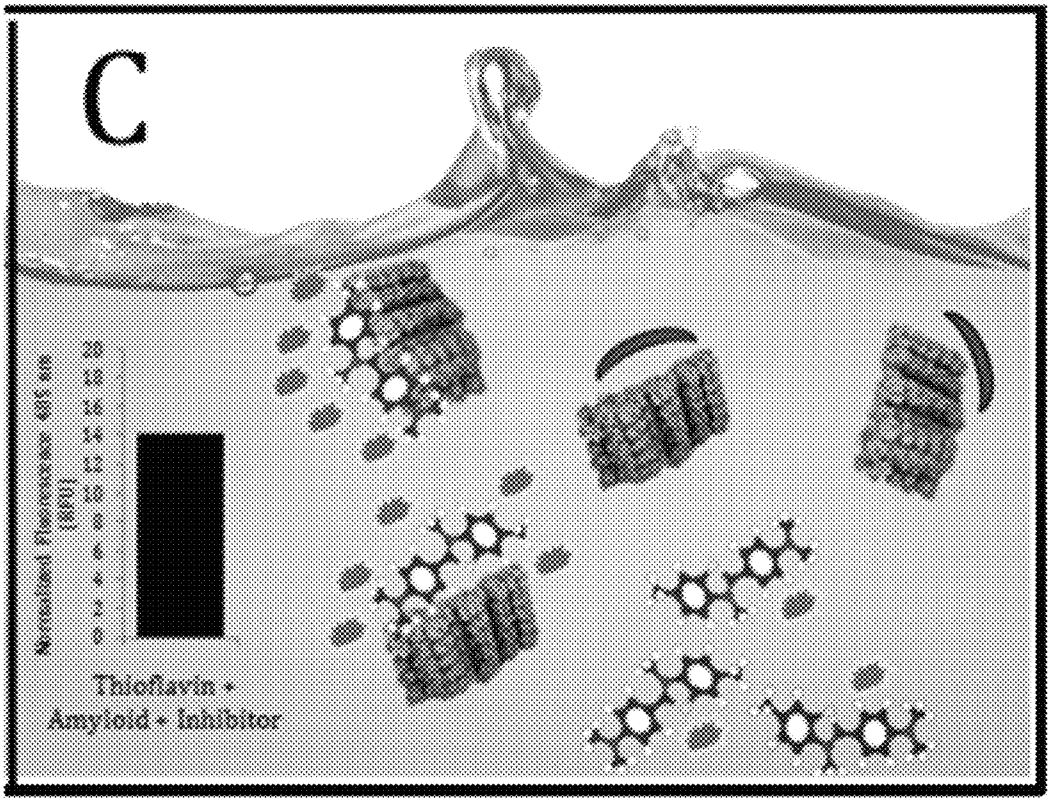

A schematic depiction of the increased fluorescence upon amyloid binding, particularly for the case of thioflavin-T, is shown in FIGS. 1A-B. As shown therein, when not bound to Abeta plaques, the dye emits a weak FL signal at a $\lambda_{max}$ of approximately 440-445 nm. However, when bound to Abeta plaque, its FL increases dramatically and results in a strong FL signal with a characteristically shifted $\lambda_{max}$ to approximately 485 nm. In view thereof, as opposed to existing methods that detect binding of the dye through increased fluorescence, the present methods identify amyloid-binding compounds through a lack of binding between the dye and the amyloid, as evidenced by attenuated fluorescence. That is, as shown in FIG. 1C, when a screened compound binds to the amyloid in the brain sample it prevents the dye from binding to the sample as well, which decreases the fluorescence signal of the dye. Accordingly, in some embodiments, the method of screening includes combining the target compound(s) with a dye (e.g., Thioflavin-T) and endogenous amyloid (e.g., endogenous amyloid-β (Abeta) plaques in the 5XFAD brain lysate), then measuring the fluorescence of the combination. In some embodiments, the fluorescence of the combination is then compared to negative and/or positive control. When the fluorescence is attenuated it indicates that the target compound(s) bound to the amyloid beta, and thus inhibited the binding of Thioflavin-T to the amyloid beta. In other words, when the fluorescence is attenuated it indicates that the target compound(s) bind amyloid beta. The larger the decrease in fluorescence signal the stronger the inhibitors.

Additionally or alternatively, in some embodiments, the method includes determining the structure-activity relationship (SAR) of the compounds. In some embodiments, the SAR study enhances the likelihood of hits and explores the untapped or underrepresented regions of chemical structure of the compounds, such as promethazine analogs. In some embodiments, this provides the promise of advancing chemical screening with the focus to enhance specificity and reducing the testing doses.

In some embodiments, the HATCO assay utilizes an endogenous source of Abeta. For example, in one embodiment, the HATCO assay uses endogenous Abeta obtained from the brains of 5XFAD mice for a large-scale HTS operation. The APP/PS1 double transgenic mouse model coexpressed five familial AD (FAD) and additively increase Abeta-42 production. This animal model expressed Abeta at 1.5 month-old, and at the age of 6 month-old, massive levels of Abeta could be found in the subiculum, CA regions and the cortex. In another embodiment, all of the brain lysate for the HTS assay was obtained from 8-month-old 5XFAD mice, and the control brain lysate was generated from age-matched wt mice. In a further embodiment, the endogenous Abeta obtained from brain lysate provides a reliable source of Abeta plaques to ensure the reproducibility of the assay. Without wishing to be bound by theory, it is believe that by selecting the library of compounds to be screened based on ideal log P values for BBB penetration, rather than structural priority similar to known Abeta-binding molecules, the HATCO assay described herein will enhance the likelihood of identifying novel Abeta-binding molecules with diverse and untapped regions of chemical structures. That is, in contrast to existing approaches, which deduce amyloid-binding molecules from other known amyloid-binding compounds, the instant approach uses the novel HTS assay to provide new scaffolds that diversify the chemical genetics of amyloid-binding molecules, thus offering the promise of advancing the chemical genetics for AD therapeutic drugs.

Figure 2:
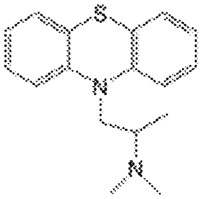
FIG. 2 shows an image illustrating the structure of N,N-dimethyl-1-(10H-phenothiazin-10-yl)propan-2-amine (Promethazine).
Figure 3:
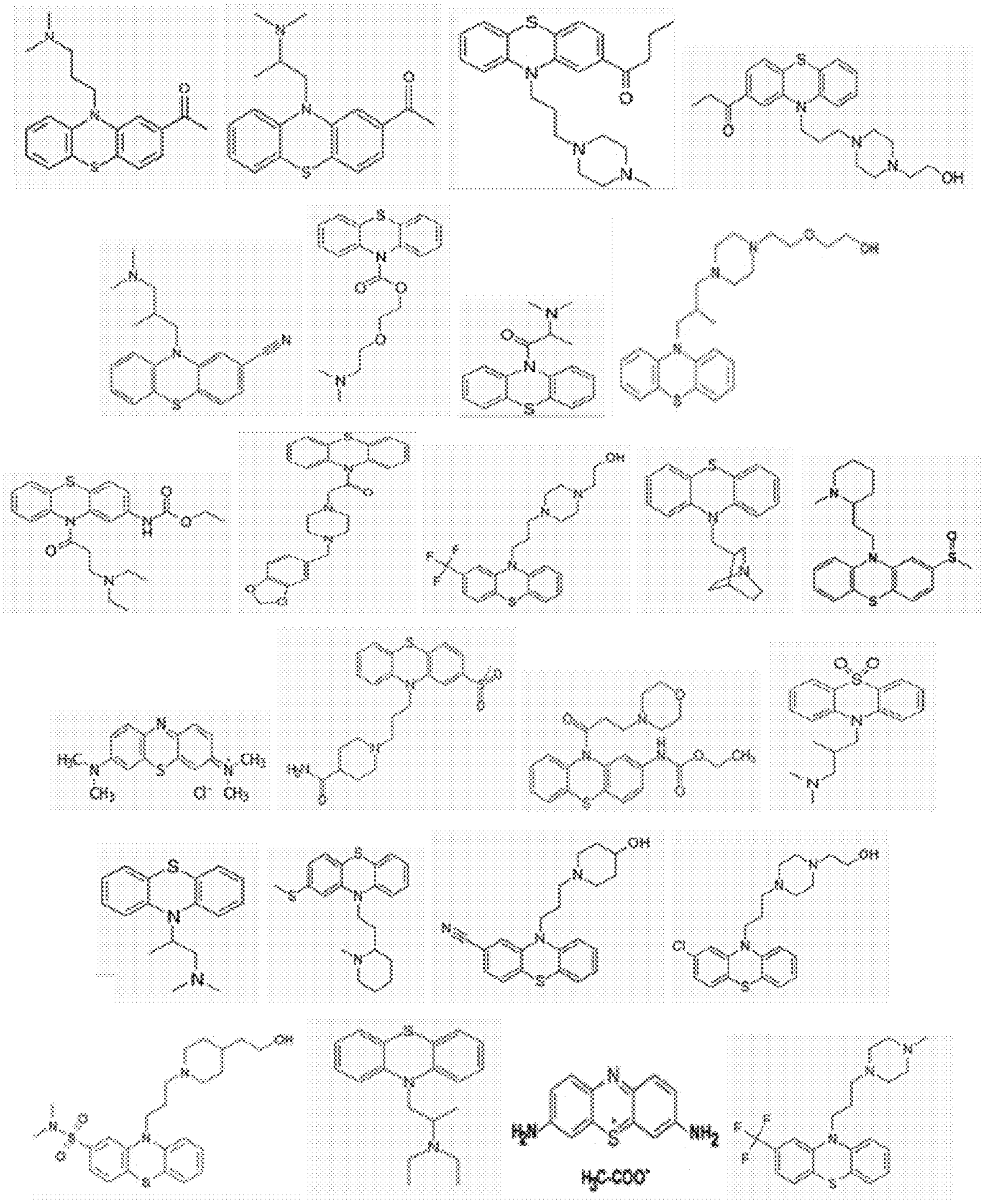
FIG. 3 shows images illustrating various phenothiazine analogs.
Figure 4A:
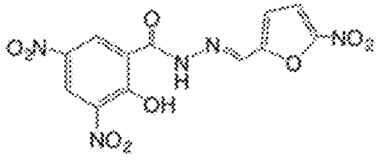
FIGS. 4A-G show images illustrating various amyloid-binding compounds. (A) 2-Hydroxy-3,5-dinitro-benzoic acid (5-nitro-furan-2-ylmethylene)-hydrazide. (B) 3-Phenylazo-pyridine-2,6-diamine (Phenazopyridine). (C) 2,4a,6a,9,10,12b,14a-Heptamethyl-11-oxo-1,2,3,4,4a,5,6,6a,11,12b,13,14,14a,14b-tetradecahydropicene-2-carbaldehyde. (D) 2,3,5,6-Tetrachloro-[1,4]benzoquinone (Chloranil). (E) 2-Hydroxy-5-[4-(pyridine-2-ylsulfamoyl)-phenylazo]-benzoic acid (Azulfidine). (F) 1,6,7,1',6',7'-Hexahydroxy-5,5'-diisopropyl-3,3'-dimethyl-[2,2']binaphthalenyl-8,8'-dicarbaldehyde (Gossypol). (G) (E)-5-(4-hydroxystyryl)benzene-1,3-diol (Resveratrol).
Figure 4B:
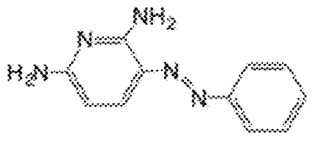
Figure 4C:
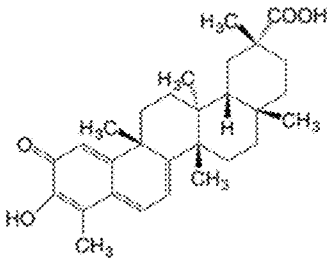
Figure 4D:
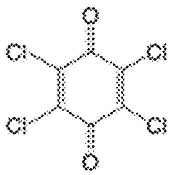
Figure 4E:
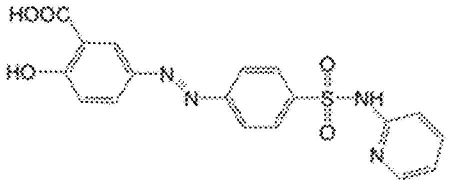
Figure 4F:
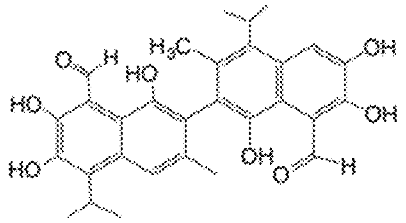
Figure 4G:
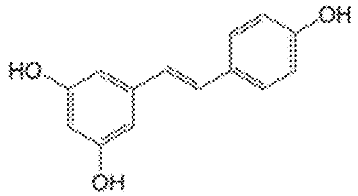

Also provided herein, in some embodiments, are amyloid-binding compounds and methods of use thereof. In some embodiments, the amyloid-binding compounds include compounds that bind amyloid-β (Abeta) plaques. For example, in one embodiment, the amyloid-binding compounds include a phenothiazine ring. In another embodiment, the amyloid-binding compound includes promethazine (FIG. 2). In a further embodiment, the compound is promethazine and/or a promethazine analog such as, but not limited to, those shown in FIG. 3. Other amyloid-binding compounds include, but are not limited to, one or more of the compounds shown in FIGS. 4A-G. In some embodiments, the amyloid-binding compound binds amyloid-β (Abeta). In some embodiments, the amyloid-binding compound binds amyloid plaques associated with Alzheimer's disease. In some embodiments, the amyloid-binding compounds cross the blood-brain-barrier in vivo and are retained in the brain in an amyloid-dependent manner.

Figure 5:
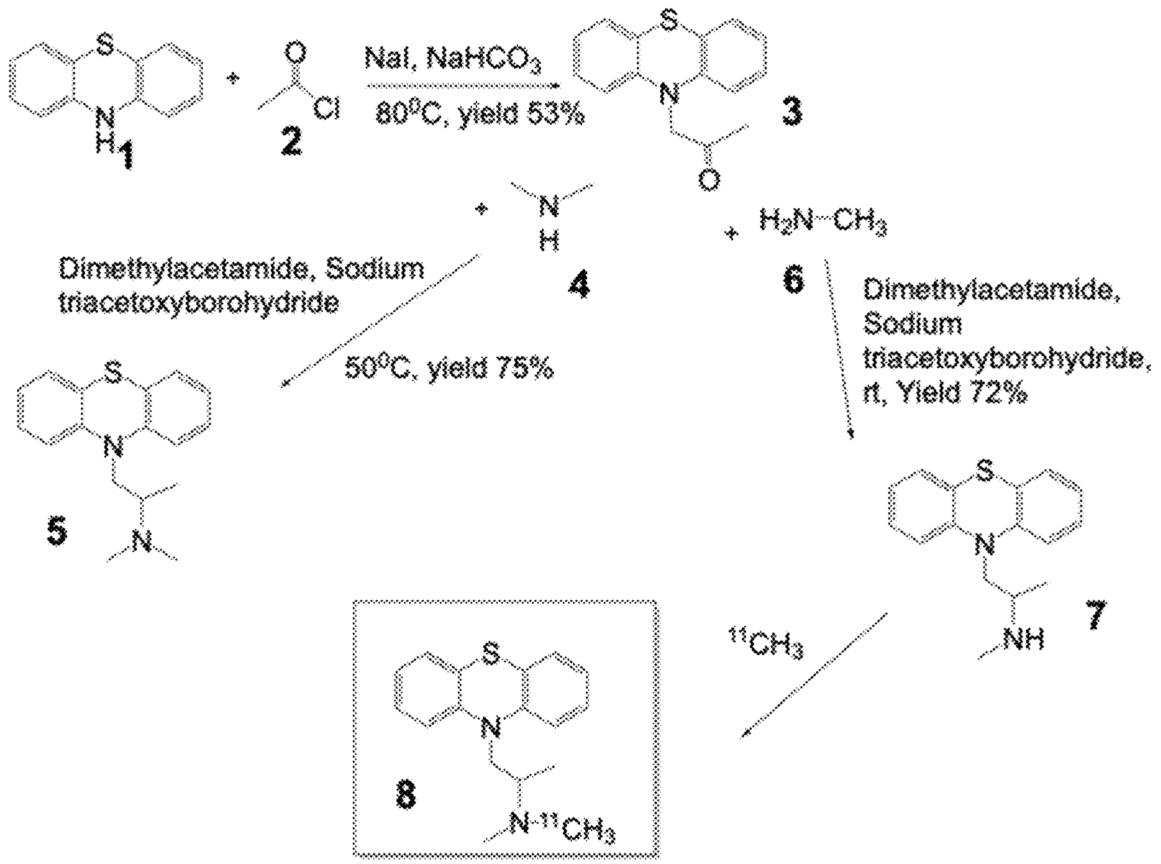
FIG. 5 shows a schematic illustrating the design and synthesis of promethazine PET probe for in vivo molecular imaging.

Further provided herein, in some embodiments, is a positron emission tomography (PET) imaging precursor and/or probe. In some embodiments, the PET imaging probe includes a PET labeled amyloid-binding compound. The PET labeled amyloid-binding compound includes any suitable amyloid-binding compound disclosed herein labeled with an isotope such as, but not limited to, [$^{11}$C]carbon, [$^{18}$F]fluoride, [$^{68}$Ga]gallium, [$^{64}$Cu]copper, or any other suitable positron emitter. In one embodiment, the PET labeled amyloid-binding compound includes phenothiazine analogs, promethazine, a promethazine analog according to FIG. 3, and/or a compound according to any of FIGS. 4A-G labeled with one or more of the isotopes disclosed herein. For example, in another embodiment, the PET labeled amyloid-binding compound includes a promethazine analog labeled with [$^{11}$C]carbon (FIG. 5). In another embodiment, the PET labeled amyloid-binding compound includes resveratrol (FIG. 4G) labeled with [$^{18}$F]fluoride. Additionally or alternatively, the PET labeled amyloid-binding compound may include any other amyloid-binding compound determined by the screening methods disclosed herein and labeled with one or more of the isotopes disclosed herein. Although discussed primarily with respect to certain isotope labeled amyloid-binding compounds, as will be appreciated by those skilled in the art, the disclosure is not so limited and may include any other suitable amyloid-binding compounds and/or isotopes.

Referring to FIG. 5, in some embodiments, a method of synthesizing the PET labeled amyloid-binding compound includes alkylation of a starting compound (e.g., FIG. 5; 1) in the presence of NaI and $NaHCO_3$ to afford an intermediate (e.g., FIG. 5; 3). Suitable starting materials include any amyloid-binding compound disclosed herein, such as, but not limited to, phenothiazine analogs, promethazine, and/or a promethazine analog. Next, the intermediate is treated with methyl amine (FIG. 5; 6) in the presence of sodium triacetoxyborohydride and dimethylacetamide at room temperature to form a precursor (FIG. 5; 7). The precursor is then labeled with the desired isotope or positron emitter. In some embodiments, this step also includes the radiochemical synthesis of the isotope, as discussed in Example 3 below. Additionally or alternatively, in some embodiments, as part of radioisotope labeling, besides making the precursors, a "cold" compound ("cold" compound is identical to radioisotope-labeled compound, albeit there is no radioisotope attached) is also developed in order to provide physical evidence to support the analytical characterization of the labeled probe. In one embodiment, rather than treating the intermediate with methyl amine, the "cold" compound is synthesized from the intermediate using dimethyl amine (FIG. 5; 4) in the presence of sodium triacetoxyborohydride and dimethylacetamide at 50° C.

Figure 6A:
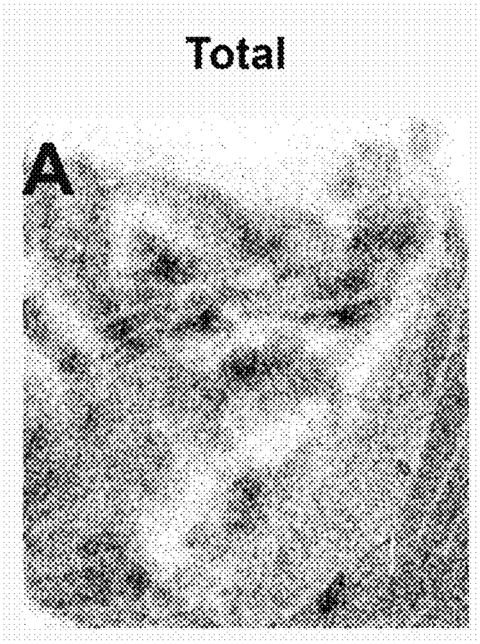
FIGS. 6A-B show images illustrating the specificity of [$^{11}$C]promethazine on binding to Abeta plaques via an autoradiography study of human brain tissues collected from patients of Alzheimer's disease. (A) Tissues (10 nm) on glass slides were soaked in [$^{11}$C]promethazine PET probe diluted in PBS solution. (B) Tissues were soaked in the same solution as (A), albeit with the presence of a large excess of "cold" (unlabeled) promethazine, denoted as PMZ in the figure.
Figure 6B:
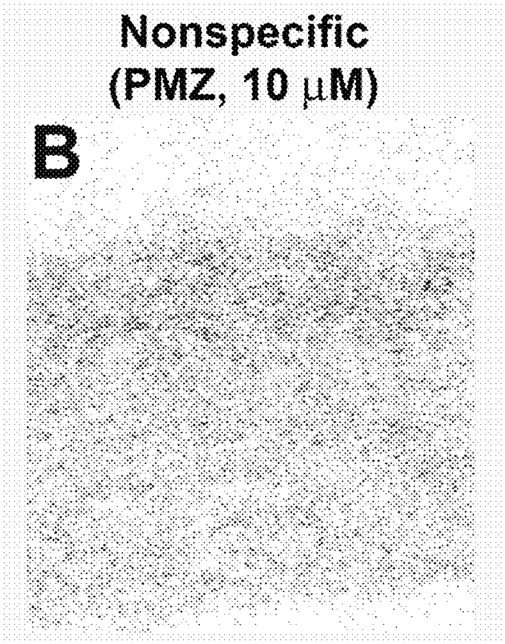

In some embodiments, the method of synthesizing the PET labeled amyloid-binding compound includes forming a [$^{18}$F]reseveratrol PET probe. In one embodiment, forming the [$^{18}$F]reseveratrol precursor includes derivatizing one of the aromatic rings of resveratrol with a good leaving group, such as —$NO_2$ or trimethylammonium triflate. In another embodiment, this precursor is then reacted with [$^{18F}$]fluoride in the presence of Kryptofix 222. Additionally or alternatively, in one embodiment, the synthesis of the resveratrol PET probe includes the use of diaryliodonium salts, which are capable of providing radiofluorination of electron-deficient, as well as electron-rich (non-activated or deactivated) arenes, with unrestricted choice of position on the rings can be achieved with this method. In such embodiments, the hypervalent iodine compounds, such as diaryliodonium salts ($Ar_2I^+X^-$) and aryliodonium ylides ($ArI^+R^-$), provide useful precursors for labeling homoarenes like reseveratrol. For example, this approach has been used to synthesize no-carrier-added cyclotron-produce [$^{18}$F]fluoride ion in the past years. Without wishing to be bound by theory, it is believed that the methods discussed herein retain the biological activity of resveratrol by forming a probe that has similar chemical structure, Also provided herein, in some embodiments, are methods of detecting amyloid-β (Abeta) plaques in a subject. In some embodiments, the method includes administering one or more of the compounds disclosed herein to a subject and then detecting the compound within the subject. In some embodiments, detecting the compounds, such as the isotope labeled amyloid-binding compounds, includes using autoradiography or any other suitable method of detecting isotope labeled compounds. For example, in one embodiment, the method includes soaking a sample, such as a brain section, in the isotope-labeled promethazine analog and then detecting the amyloid-β (Abeta) plaques via the labeled promethazine analog using autoradiography (FIGS. 6A-B). In another embodiment, the non-labeled promethazine analog crosses the blood-brain-barrier after intravenous administration and subsequently binds to amyloid beta and/or amyloid plaques. In such embodiments, the promethazine analog is retained in the brain of the subject in an amyloid-dependent manner such that the detection of the promethazine analog using matrix-assisted laser desorption/ionization imaging mass spectrometry (MALDI-IMS) indicates the amount and/or location of amyloid beta and/or amyloid plaques in the brain. Accordingly, in some embodiments, the method also includes detection of amyloid plaques in a subject's brain and determining whether the subject has and/or is at risk for developing Alzheimer's disease or any other disease associated with Abeta plaque formation in the brain.

The presently-disclosed subject matter is further illustrated by the following specific but non-limiting examples. The following examples may include compilations of data that are representative of data gathered at various times during the course of development and experimentation related to the presently-disclosed subject matter.

EXAMPLES

Example 1

This Example discusses a robust and scalable high-throughput compatible assay for screening Abeta-binding compounds.

A robust fluorescent readout assay using topologically-sensitive dyes improves the screening of novel amyloid-binding molecules. One of the key components that make this assay more realistic is the use of endogenous amyloid obtained from 5XFAD mouse brains. The assay conditions were optimized for high throughput screening operation with Z-prime values >0.6. Using a combination library of 3,500 compounds including known drugs, natural-derived molecules, and random organic molecules, 8 unique molecules were identified as potential amyloid-binding agents.

Results

Figure 7:
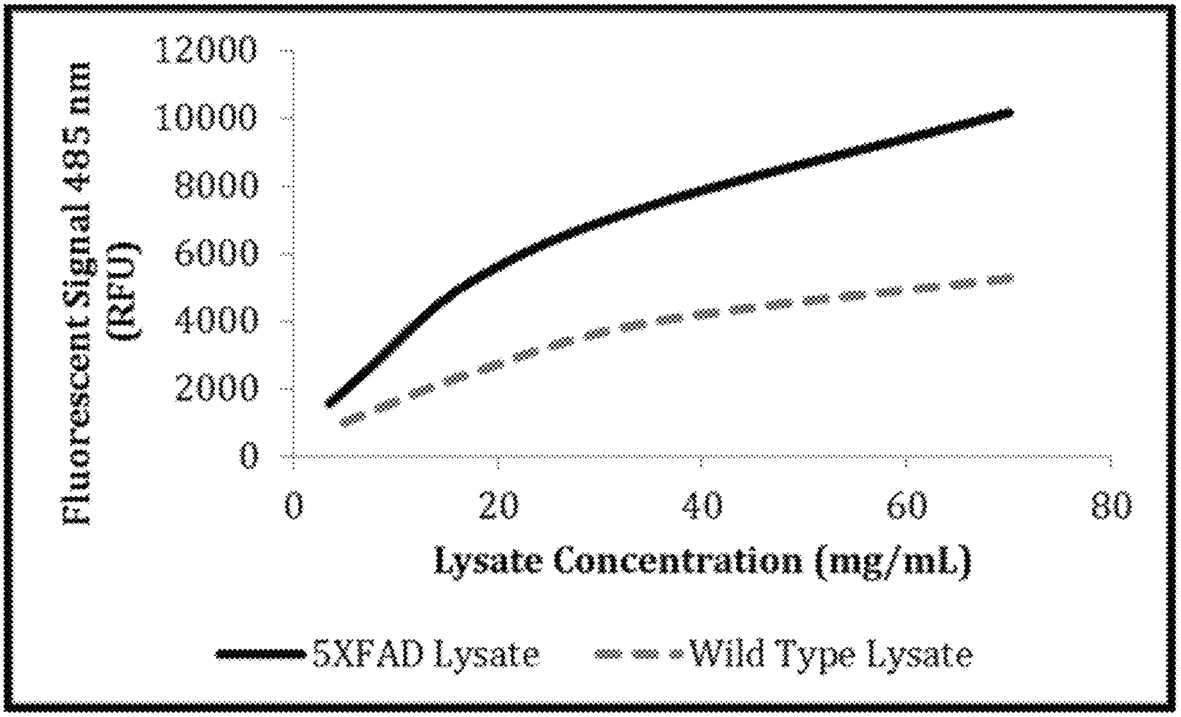
FIG. 7 shows a graph illustrating that the FL signal intensity of Thioflavin-T was enhanced in proportion to the increasing concentration of 5XFAD brain lysate.

The quality of brain lysate as a source of Abeta. The HATCO assay relies on specific interaction between thioflavin-T and Abeta present in the 5XFAD brain lysate resulting in a significantly dynamic signal change. Questions remain over whether small amount of brain lysate has enough Abeta to activate the signal or whether other proteins in the brain may also have affinity for thioflavin-T, thus producing false-positive signals. To answer these fundamental questions, serial dilutions of 5XFAD and wt brain lysates were incubated with thioflavin-T. As depicted graphically in FIG. 7, the FL at 485 nm emanated from thioflavin-T among the dilutions of 5XFAD are consistently higher than that found in wt counterparts. Further, the signal was reciprocal to the concentration of brain lysate. It is noteworthy that the concentration of the brain lysate in each assay was quantified by BCA assay and distributed equally as designated in each well during the assay. During the validation process, over 50 different batches of mouse brain lysates were prepared, tested, and confirmed this observation, demonstrating the robustness, reliability and reproducibility of using 5XFAD brain lysate.

Figure 8:
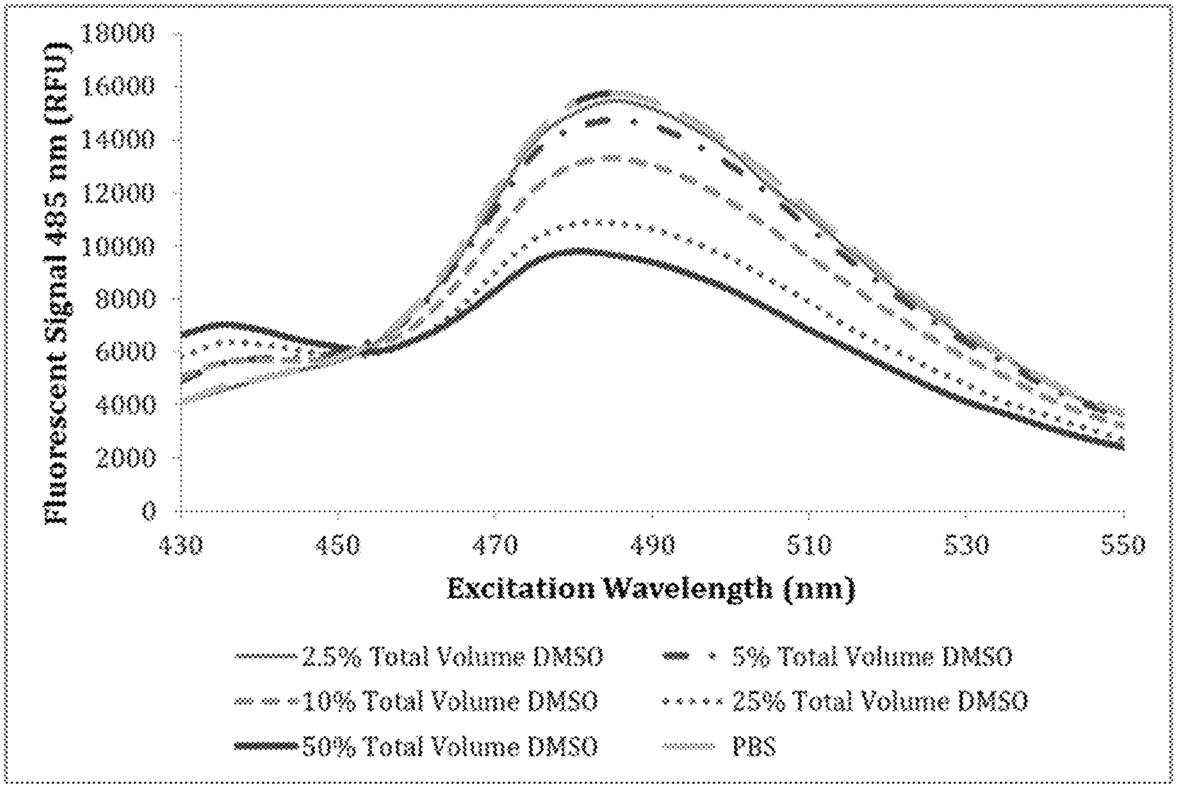
FIG. 8 shows a graph illustrating the solvent effects of the HATCO assay. DMSO was included in the assay from 2.5%-50% of total volume. For each of these conditions, a FL profile secondary to excitation at 410 nm was collected on the sample across an emission range of 430-550 nm.

Solvent effect. During the course of work, it was realized that although DMSO is a great solvent for amphiphilic molecules, which have structurally diverse functional groups, the major concern regarding the use of DMSO is the potential perturbation of the inter-molecular binding since it is an amphiphile. To address this concern, the proportion of DMSO was incrementally increased in the HATCO assay from 2.5% to 50% of the assays total volume. For example, in a 2.5% total volume condition, 625 nanoliters of DMSO was added to 20 μL of 5XFAD lysate (5 mg/mL) and 5 μL of thioflavin-T (10 μM). Similarly for the 50% total volume DMSO condition, 12.5 μL of DMSO was added to the same volumes of Abeta-containing lysate and thioflavin-T. As graphically illustrated in FIG. 8, the inclusion of DMSO in the assay attenuates thioflavin-T fluorescence at 485 nm in a dose-dependent manner. Negligible loss of Abeta-specific thioflavin-T signal at 485 nm up to 5% total volume of DMSO, with a dose-dependent decrease in signal at increasing higher concentrations. Cumulatively, the result suggests that the HATCO assay is compatible with the use of DMSO as a solvent up to a threshold tolerance 5% of the assay's total volume.

Figure 9:
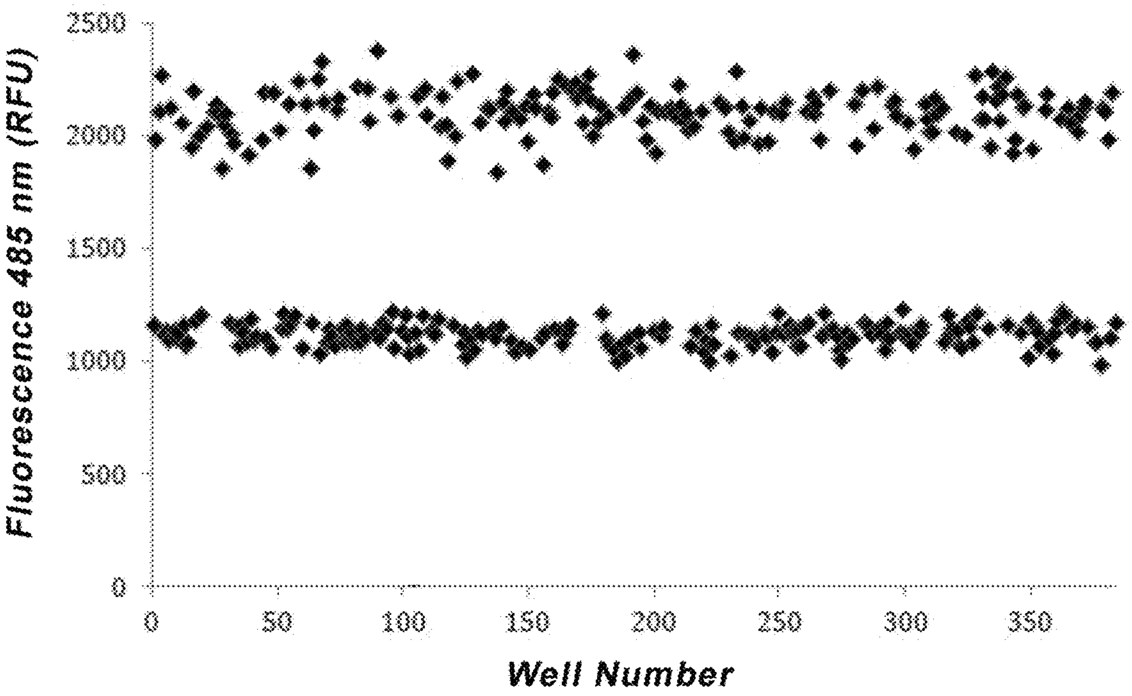
FIG. 9 shows a graph illustrating a scatter plot of the emission at 485 nm of Thioflavin-T measured from 384-well plate loaded with Thioflavin-T alone or Thioflavin-T with 5XFAD brain lysate corresponding to "min-max" conditions, respectively in a checkerboard pattern. The Z-prime values were assessed along with variations.

The HATCO assay can be optimized for HTS operation. The quality of the HATCO assay was assessed using the Z' value via triplicate 384-well plates in order to predict if it is suitable for a HTS setting. In this assay, all components of the assay were scaled down in term of volume and the precision optimized using the BRAVO liquid handling system; all dispensing operations were double-checked to ensure no presence of microdroplets on the pipette tips that might resulting in some outliers among the sample leading to an apparent unfavorable Z-factor. All wells were added with equal amount of brain lysate (5 mg/mL; 20 μL) followed by thioflavin-T (10 μM, 5 μL). In a typical "min-max" experiment in a checkerboard pattern, the wells correspond to "min" value contained only Thioflavin-T (control, in FIG. 9). The "max" wells contained brain lysates and Thioflavin-T. One of the first tasks was to determine the optimal incubation time and it was found that after incubation, it was possible to not only can get ideal "min-max" values, but the p values are also remarkable at Z'-prime values >0.6 and a coefficient of variation ~4%. In this scale screening of 3,500 compounds using eleven 384-well plates, in which overall average Z-prime value for 11 plates was 0.6215.

HATCO assay reveals novel Abeta-binding compounds. Using the optimized assay conditions a library of 3500 structurally diverse compounds with diverse chemical constituents and classifications was screened, including of which 50% are FDA-approved drugs, 30% natural products and 20% random bioactively organic compounds. Through the assay, 44 hit compounds were identified in the primary screen (TABLE 1).

TABLE 1

Primary hit compounds identified after employing a single-dose HATCO assay.

| | Structure | ID | MW (g/mol) | Clogp | Common name | Tpsa | ALOGP |
|---|---|---|---|---|---|---|---|
| 1 | 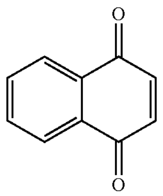 [SMILES: O=C1C=CC(=O)c2ccccc21] | VU0656808 | 158.16 | 1.45 | | 34.14 | 1.76 |
| 2 | 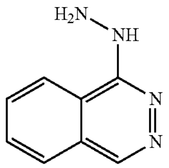 [SMILES: NNc1nncc2ccccc12] | VU0244461 | 160.18 | 0.67 | Hydralazine | 63.83 | 0.94 |
| 3 | 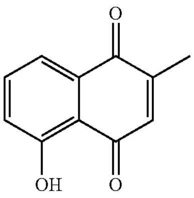 | VU0243610 | 188.18 | 1.17 | Plumbagin | 54.37 | 1.96 |

TABLE 1-continued
Primary hit compounds identified after employing a single-dose HATCO assay.
| | Structure | ID | MW (g/mol) | Clogp | Common name | Tpsa | ALOGP |
|---|---|---|---|---|---|---|---|
| 4 | 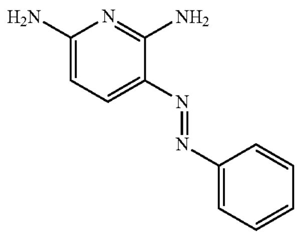 [SMILES: Nc1ccc(/N=N/c2ccccc2)c(N)n1] | VU0244402 | 213.24 | 2.69 | Phenazopyridine | 89.65 | 2.63 |
| 5 | 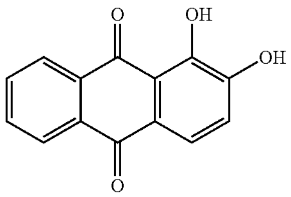 [SMILES: O=C1c2ccccc2C(=O)c2c1ccc(O)c2O] | VU0005325 | 240.21 | 2.74 | Alizarin | 74.60 | 2.32 |
| 6 | 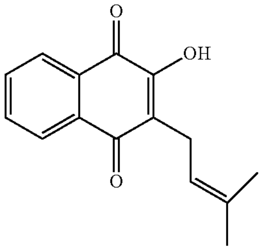 [SMILES: CC(C)=CCC1=C(O)C(=O)c2ccccc2C1=O] | VU0244310 | 242.27 | 3.36 | Lapachol | 54.37 | 3.04 |
| 7 | 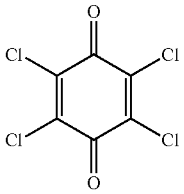 [SMILES: O=C1C(Cl)=C(Cl)C(=O)C(Cl)=C1Cl] | VU0243635 | 245.88 | 1.87 | Chloranil | 34.14 | 2.16 |
| 8 | 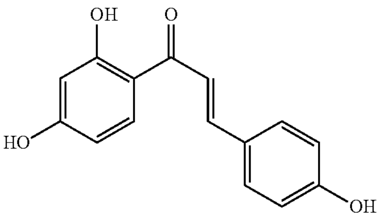 [SMILES: O=C(/C=C/c1ccc(O)cc1)c1ccc(O)cc1O] | VU0243638 | 256.26 | 2.64 | Isoliquiritingenin | 77.76 | 2.98 |
| 9 | 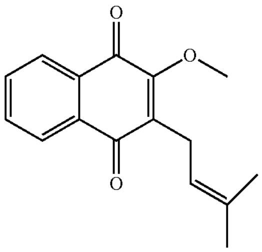 [SMILES: COC1=C(CC=C(C)C)C(=O)c2ccccc2C1=O] | VU0656769 | 256.30 | 3.24 | | 43.37 | 3.26 |

TABLE 1-continued
Primary hit compounds identified after employing a single-dose HATCO assay.
| | Structure | ID | MW (g/mol) | Clogp | Common name | Tpsa | ALOGP |
|---|---|---|---|---|---|---|---|
| 10 | 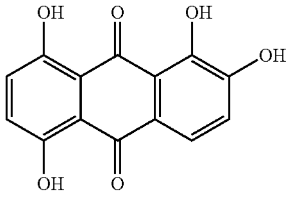 [SMILES: O=C1c2ccc(O)c(O)c2C(=O)c2c(O)ccc(O)c21] | VU0243022 | 272.21 | −0.15 | 1,2,5,8-tetrahydroxy anthraquinone | 115.06 | 1.84 |
| 11 | 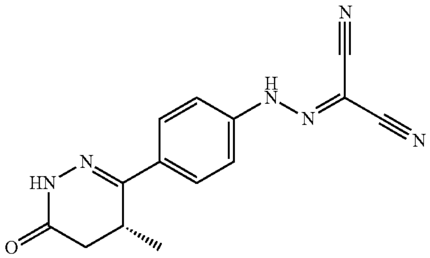 [SMILES: C[C@@H]1CC(=O)NN=C1c1ccc(NN=C(C#N)C#N)cc1] | VU0656154 | 280.29 | 2.44 | Levosimendan | 113.43 | 1.49 |
| 12 | 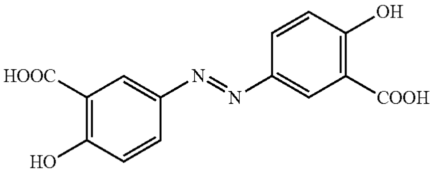 [SMILES: O=C(O)c1cc(/N=N/c2ccc(O)c(C(=O)O)c2)ccc1O] | VU0656169 | 300.23 | 3.11 | | 145.44 | 0.026 |
| 13 | 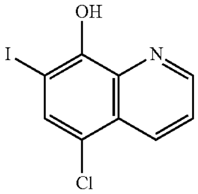 [SMILES: Oc1c(I)cc(Cl)c2cccnc12] | VU0239562 | 305.50 | 3.40 | Clioquinol | 33.12 | 3.02 |
| 14 | 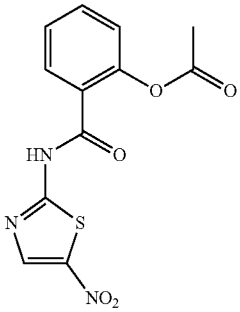 [SMILES: CC(=O)Oc1ccccc1C(=O)Nc1ncc([N+](=O)[O-])s1] | VU0254295 | 307.28 | 1.22 | Nitazoxanide | 114.11 | 1.40 |
| 15 | 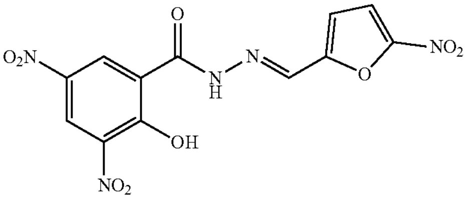 [SMILES: O=C(N/N=C/c1ccc([N+](=O)[O-])o1)c1cc([N+](=O)[O-])cc([N+](=O)[O-])c1O] | VU0656139 | 365.21 | 2.54 | | 212.29 | 1.64 |

TABLE 1-continued
Primary hit compounds identified after employing a single-dose HATCO assay.
| | Structure | ID | MW (g/mol) | Clogp | Common name | Tpsa | ALOGP |
|---|---|---|---|---|---|---|---|
| 16 | 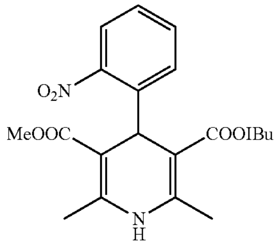 | VU0243156 | 388.42 | 3.03 | Nisoldipine | 110.45 | 2.96 |
| 17 | 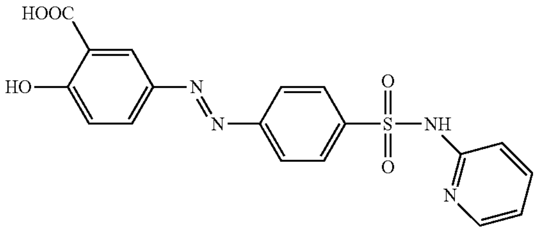 [SMILES: O=C(O)c1cc(/N=N/c2ccc(S(=O)(=O)Nc3ccccn3)cc2)ccc1O] | VU0243360 | 398.40 | 4.51 | Azulfidine | 141.31 | 3.46 |
| 18 | 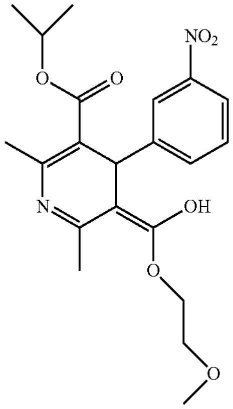 [SMILES: COCCO/C(O)=C1\C(C)=NC(C)=C(C(=O)OC(C)C)C1c1cccc([N+](=O)[O-])c1] | VU0239603 | 418.45 | 2.73 | Nimodipine | 123.17 | 2.88 |
| 19 | 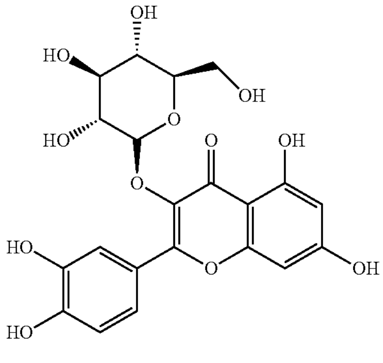 | VU0424052 | 464.38 | | | | −0.3 |

TABLE 1-continued
Primary hit compounds identified after employing a single-dose HATCO assay.
| | Structure | ID | MW (g/mol) | Clogp | Common name | Tpsa | ALOGP |
|---|---|---|---|---|---|---|---|
| 20 | 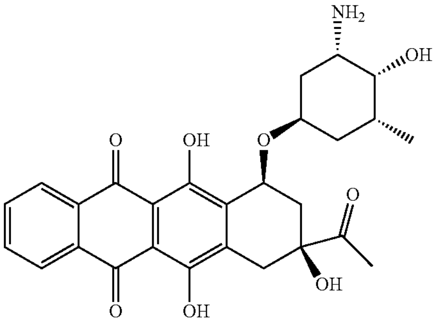 [SMILES: CC(=O)[C@]1(O)Cc2c(O)c3c(c(O)c2[C@@H](O[C@@H]2C[C@@H](C)[C@@H](O)[C@@H](N)C2)C1)C(=O)c1ccccc1C3=O] | VU0254343 | 497.50 | 0.32 | Idarubicin | 176.61 | 0.64 |
| 21 | 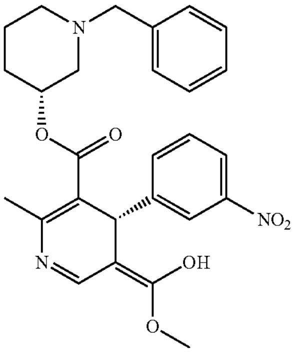 [SMILES: CO/C(O)=C1\C=NC(C)=C(C(=O)O[C@@H]2CCCN(Cc3ccccc3)C2)[C@@H]1c1cccc([N+](=O)[O-])c1] | VU0253939 | 505.57 | 4.13 | | 117.18 | 4.49 |
| 22 | 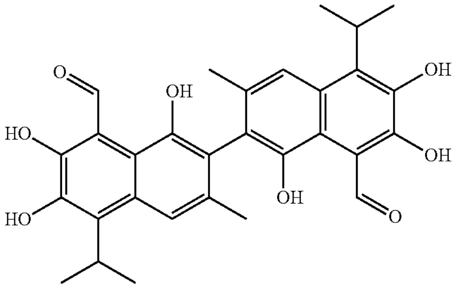 [SMILES: Cc1cc2c(C(C)C)c(O)c(O)c(C=O)c2c(O)c1-c1c(C)cc2c(C(C)C)c(O)c(O)c(C=O)c2c1O] | VU0243640 | 518.56 | 3.86 | Gossypol | 155.52 | 6.60 |
| 23 | 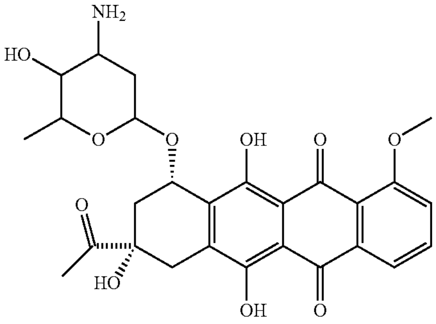 [SMILES: COc1cccc2c1C(=O)c1c(O)c3c(c(O)c1C2=O)C[C@@](O)(C(C)=O)C[C@@H]3OC1CC(N)C(O)C(C)O1] | VU0465285 | 527.53 | 0.22 | Daunorubicin | 185.84 | 0.63 |

TABLE 1-continued
Primary hit compounds identified after employing a single-dose HATCO assay.
| | Structure | ID | MW (g/mol) | Clogp | Common name | Tpsa | ALOGP |
|---|---|---|---|---|---|---|---|
| 24 | 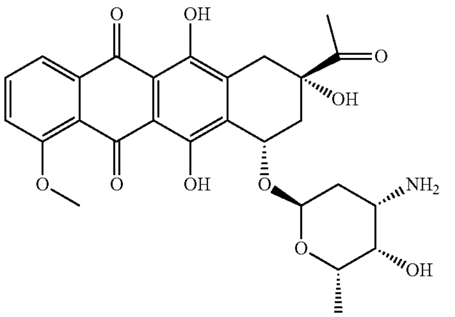 [SMILES: COc1cccc2c1C(=O)c1c(O)c3c(c(O)c1C2=O)C[C@@](O)(C(C)=O)C[C@@H]3O[C@H]1C[C@H](N)[C@H](O)[C@H](C)O1] | VU0656003 | 527.53 | 0.22 | Daunorubicin | 185.84 | 0.63 |
| 25 | 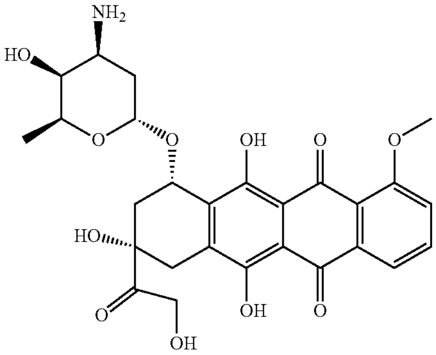 [SMILES: COc1cccc2c1C(=O)c1c(O)c3c(c(O)c1C2=O)C[C@@](O)(C(=O)CO)C[C@@H]3O[C@H]1C[C@H](N)[C@H](O)[C@H](C)O1] | VU0239546 | 543.52 | −0.38 | Doxorubicin | 206.07 | −0.04 |
| 26 | 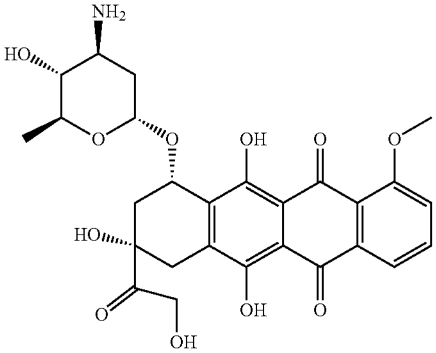 [SMILES: COc1cccc2c1C(=O)c1c(O)c3c(c(O)c1C2=O)C[C@@](O)(C(=O)CO)C[C@@H]3O[C@H]1C[C@H](N)[C@@H](O)[C@H](C)O1] | VU0424047 | 543.52 | −0.38 | | 206.07 | −0.04 |
| 27 | 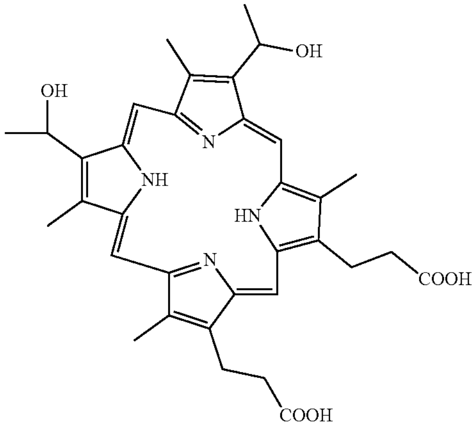 [SMILES: CC1=C(CCC(=O)O)c2cc3[nH]c(cc4nc(cc5[nH]c(cc1n2)c(C)c5C(C)O)C(C)=C4C(C)O)c(C)c3CCC(=O)O] | VU024454 | 598.70 | 0.75 | Haemato-porphyrin | 172.42 | 6.96 |

TABLE 1-continued
Primary hit compounds identified after employing a single-dose HATCO assay.
| | Structure | ID | MW (g/mol) | Clogp | Common name | Tpsa | ALOGP |
|---|---|---|---|---|---|---|---|
| 28 | 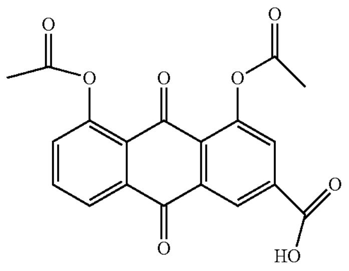 [SMILES: CC(=O)Oc1cccc2c1C(=O)c1c(OC(C)=O)cc(C(=O)O)cc1C2=O] | VU0239662 | 368.30 | 2.34 | | 124.04 | 1.97 |
| 29 | 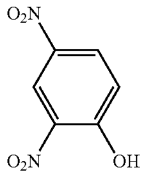 | VU0243418 | 184.11 | 1.83 | | 111.87 | 1.376 |
| 30 | 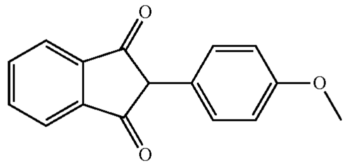 [SMILES: COc1ccc(C2C(=O)c3ccccc3C2=O)cc1] | VU0243421 | 252.27 | 2.58 | | 43.37 | 2.803 |
| 31 | 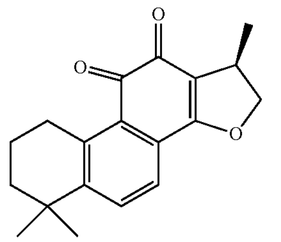 [SMILES: C[C@H]1COC2=C1C(=O)C(=O)c1c2ccc2c1CCCC2(C)C] | VU0243646 | 296.37 | 4.08 | | 43.37 | 3.76 |
| 32 | 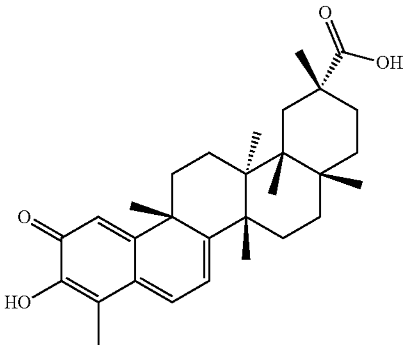 | VU0243664 | 450.62 | 5.85 | | 74.6 | 5.48 |
| 33 | 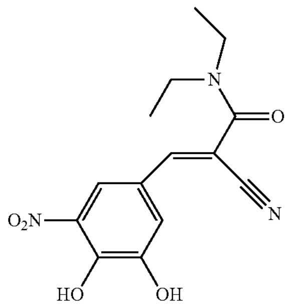 [SMILES: CCN(CC)C(=O)/C(C#N)=C/c1cc(O)c(O)c([N+](=O)[O-])c1] | VU0518361 | 305.29 | 2.41 | | 130.38 | 1.66 |

TABLE 1-continued
Primary hit compounds identified after employing a single-dose HATCO assay.
| | Structure | ID | MW (g/mol) | Clogp | Common name | Tpsa | ALOGP |
|---|---|---|---|---|---|---|---|
| 34 | 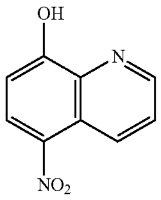 [SMILES: O=[N+]([O-])c1ccc(O)c2ncccc12] | VU0254088 | 190.16 | 1.61 | | 78.94 | 1.67 |
| 35 | 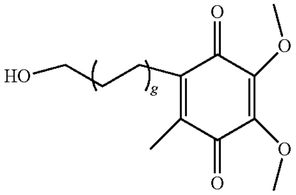 | VU0254117 | 338.44 | 3.59 | | 72.83 | 3.84 |
| 36 | 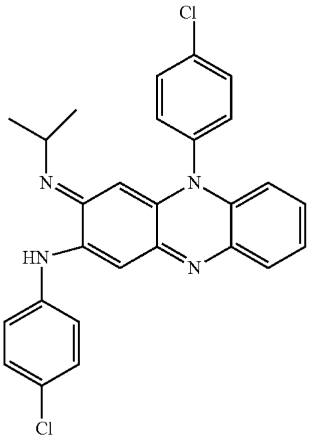 [SMILES: CC(C)/N=c1\cc2n(-c3ccc(Cl)cc3)c3ccccc3nc-2cc1Nc1ccc(Cl)cc1] | VU0424095 | 473.41 | 7.05 | | 39.99 | 7.14 |
| 37 | 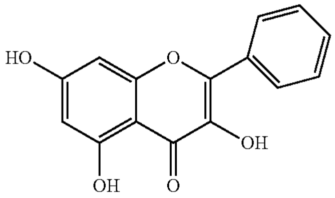 [SMILES: O=c1c(O)c(-c2ccccc2)oc2cc(O)cc(O)c12] | VU0656634 | 270.24 | 3.16 | | 86.99 | 2.11 |
| 38 | 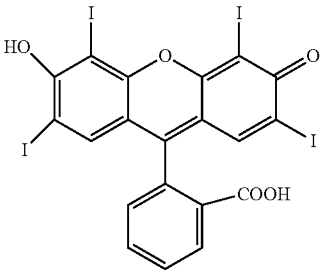 [SMILES: O=C(O)c1ccccc1-c1c2cc(I)c(=O)c(I)c-2oc2c(I)c(O)c(I)cc12] | VU0656374 | 833.88 | 6.30 | | 89.49 | 2.60 |
| 39 | 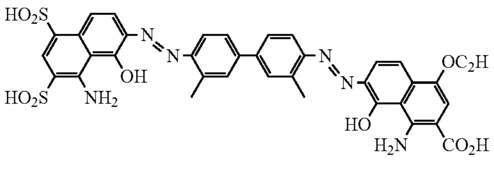 | VU0656445 | 868.85 | 3.09 | | 376.4 | −2.75 |

TABLE 1-continued

Primary hit compounds identified after employing a single-dose HATCO assay.

| | Structure | ID | MW (g/mol) | Clogp | Common name | Tpsa | ALOGP |
|---|---|---|---|---|---|---|---|
| 40 | 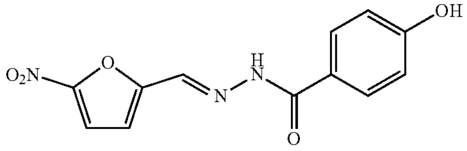 [SMILES: O=C(N/N=C/c1ccc([N+](=O)[O-])o1)c1ccc(O)cc1] | VU0656568 | 275.22 | 2.32 | | 120.65 | 1.86 |
| 41 | 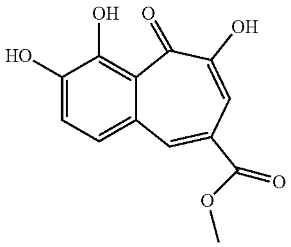 [SMILES: COC(=O)c1cc(O)c(=O)c2c(O)c(O)ccc2c1] | VU0656659 | 262.22 | 1.90 | | 104.06 | 1.13 |
| 42 | 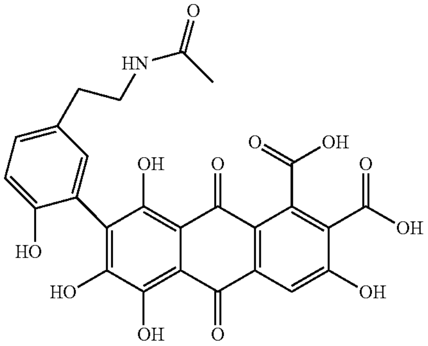 [SMILES: CC(=O)NCCc1ccc(O)c(-c2c(O)c(O)c3c(c2O)C(=O)c2c(cc(O)c(C(=O)O)c2C(=O)O)C3=O)c1] | VU0656668 | 537.43 | 0.31 | | 238.99 | 1.82 |
| 43 | 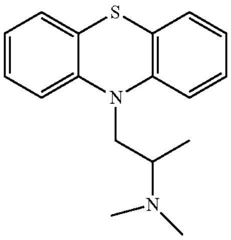 [SMILES: CC(CN1c2ccccc2Sc2ccccc21)N(C)C] | (a) | 284.42 | 4.35 | Promethazine | 31.8 | 4.40 |
| 44 | 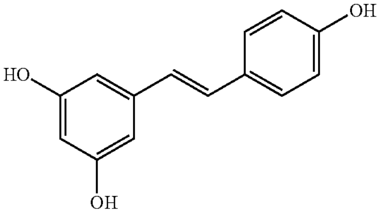 [SMILES: Oc1ccc(/C=C/c2cc(O)cc(O)c2)cc1] | (a) | 228.25 | 2.83 | Resveratrol | 60.69 | 3.06 |

HATCO competitive binding study. After primary and cross-screening experiments, only 15 compounds were qualified for the next screening operation involving competition binding assays, in which many and various concentrations of a putative hit compound ranging from 15-300 nM was tested as described in the primary assay, albeit in a duplicate fashion using the 384-well format. The addition of increasing concentrations of identified lead compounds to a mixture of fixed amount of brain lysate and thioflavin-T resulted in a dose-dependent decrease in fluorescence. To facilitate the generation of concentration-response curves, fluorescence at each data point was averaged on a compound-by-compound basis and plotted as a function of concentration. As expected, plotting of the resultant fluorescence data as a function of concentration in a logarithmic fashion revealed the characteristic sigmoidal curve. From this curve, IC50 values for each compound were calculated by fitting the data to a 4-parameter logistical model in the GraphPad software package. Overall, 8 compounds were identified as having potentials for use as Abeta-binding agents (Table 2).

TABLE 2

Abeta-binding molecules identified from HATCO assay after screening 3,500 compounds.

| Chemical Structure | Chemical Name | $IC_{50}$ (μM) | MW (g/mol) | CLogP |
|---|---|---|---|---|
| 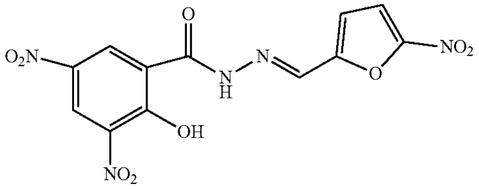 [SMILES: O=C(N/N=C/c1ccc([N+](=O)[O-])o1)c1cc([N+](=O)[O-])cc([N+](=O)[O-])c1O] | 2-Hydroxy-3,5-dinitro-benzoic acid (5-nitro-furan-2-ylmethylene)-hydrazide | 61.23 | 365.21 | 2.40 |
| 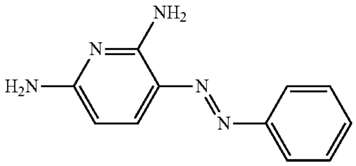 [SMILES: Nc1ccc(/N=N/c2ccccc2)c(N)n1] | 3-Phenylazo-pyridine-2,6-diamine (Phenazopyridine) | 74.29 | 213.24 | 2.05 |
| 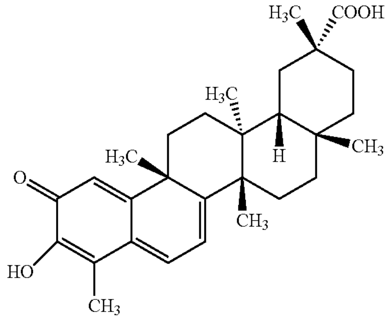 | 2,4a,6a,9,10,12b,14a-Heptamethyl-11-oxo-1,2,3,4,4a,5,6,6a,11,12b,13,14,14a,14b-tetradecahydropicene-2-carbaldehyde | 108.52 | 481.69 | 6.82 |
| 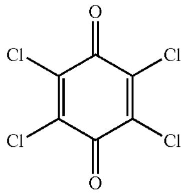 [SMILES: O=C1C(Cl)=C(Cl)C(=O)C(Cl)=C1Cl] | 2,3,5,6-Tetrachloro-[1,4]benzoquinone (Chloranil) | 90.85 | 245.88 | 3.3 |
| 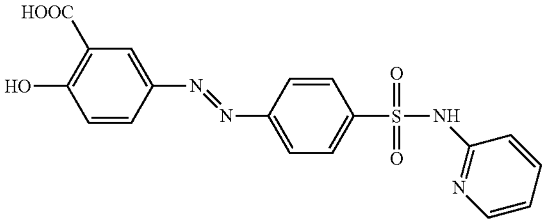 [SMILES: O=C(O)c1cc(/N=N/c2ccc(S(=O)(=O)Nc3ccccn3)cc2)ccc1O] | 2-Hydroxy-5-[4-(pyridine-2-ylsulfamoyl)-phenylazo]-benzoic acid (Azulfidine) | 68.07 | 398.39 | 3.88 |
| 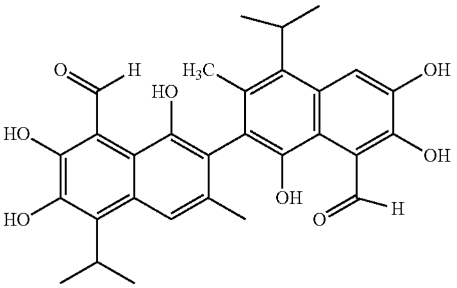 [SMILES: Cc1cc2c(C(C)C)c(O)c(O)c(C=O)c2c(O)c1-c1c(C)c(C(C)C)c2cc(O)c(O)c(C=O)c2c1O] | 1,6,7,1',6',7'-Hexahydroxy-5,5'-diisopropyl-3,3'-dimethyl-[2,2']binaphthalenyl-8,8'-dicarbaldehyde (Gossypol) | 84.17 | 518.55 | 5.36 |

TABLE 2-continued

| Abeta-binding molecules identified from HATCO assay after screening 3,500 compounds. | | | | |
|---|---|---|---|---|
| Chemical Structure | Chemical Name | $IC_{50}$ (μM) | MW (g/mol) | CLogP |
| 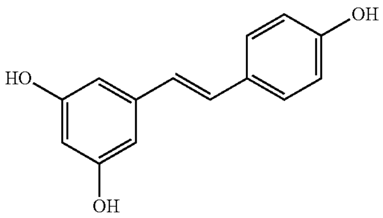 [SMILES: Oc1ccc(/C=C/c2cc(O)cc(O)c2)cc1] | (E)-5-(4-hydroxystyryl)benzene-1,3-diol (Resveratrol) | N/A | 228.25 | 2.83 |
| 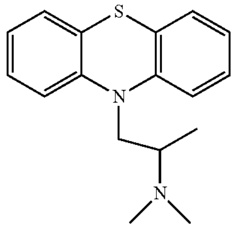 [SMILES: CC(CN1c2ccccc2Sc2ccccc21)N(C)C] | N,N-dimethyl-1-(10H-phenothiazin-10-yl)propan-2-amine (Promethazine) | 53.63 | 284.42 | 4.89 |

Discussion

Since the arrival of the Abeta cascade hypothesis as a potential mechanism of AD proposed over 26 years ago, only a small number of Abeta-binding molecules were identified. Some have been tested in clinical trials as contrast agents, while others were solely used in vitro due to poor BBB penetration. Since then, additional new Abeta-binding molecules were derived, albeit based on structural assimilation deduced from known compounds. This practice greatly limits the search for other chemical structures other than a few familiar Abeta binding motifs, via aromatic pi-stacking, or chemical structures, such as naphthalene or benzothiazole. The random screening of a large library of compounds with ideal BBB penetrant characteristics using endogenous Abeta source from the brain lysate not only facilitates the identification of novel chemical motifs but it also maximizes the chance for the hit compounds to be translated for in vivo applications. The work also addresses the common reproducibility issues of generating Abeta plaques using peptides in vitro via nucleation-polymerization process, which is stochastic in character and strongly affected by nonspecific interaction.

Figure 10:
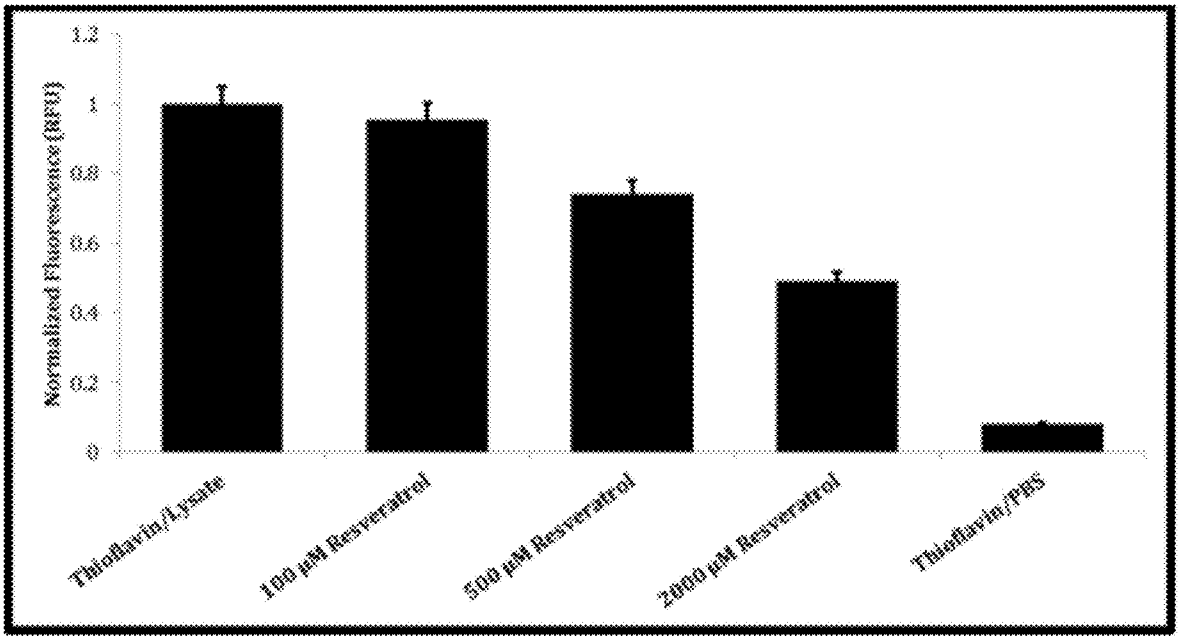
FIG. 10 shows a graph illustrating that resveratrol attenuates Abeta-specific Thioflavin-T FL at 485 nm in a dose-dependent manner.

The HATCO HTS assay successfully identified a number of new and known compounds, which have diverse chemical structures with Abeta-binding capability. Specifically, the unique ring structures of these molecules distinguish themselves from furan, benzoquinone, pyridine or stilbene rings, usually found in most Abeta-binding molecules. The ability of the hit compounds to inhibit thioflavin-T from binding to Abeta resulted in significantly attenuated FL signal as defined in the HATCO assay was confirmed based on repeated triplicate assays. As expected, the $IC_{50}$ values obtained from this assay are unsuitable for immediate future therapeutic plans, but rather, the potential lead compounds require further structure activity relationship (SAR) studies for optimization. Interestingly, the assay also showed that resveratrol, a chemical found in red wine also exhibits Abeta binding capability in a concentration-dependent manner (FIG. 10); the FL signal of thioflavin-T at 485 nm was reduced 4.4%, 25.9% and 51% at 100, 500 and 2000 μM, respectively. This observation is in line with previously reported data demonstrating the role of resveratrol in modulating Abeta levels in patients with AD. Although, it has modest $IC_{50}$ values (data not shown), the benefit of consuming natural products through healthy diets gains more ground in the campaign to prevent AD. Another notable message about this work is that the screened compounds have been preselected with ideal log p values, thus identifying hits are BBB penetrants suitable for immediate in vivo assessment. In support of this, promethazine was tested further through in vivo experiments to demonstrate that the agent identified from the HATCO assay could cross the BBB and be retained in the amyloid-burdened brain compared to normal brain, and that its distribution within the brain corroborates with that of amyloid plaques.

In conclusion, the data in this Example suggest that the HATCO assay is simple though robust and reliable. Additionally, it can be used for screening a large library of compounds. Without wishing to be bound by theory, it is believed that screening compounds for the brain, as shown in this Example, is more challenging than others because one would have to face the solubility issues. This assay overcomes those challenges to identify Abeta-binding molecules and facilitate the development of a new generation of therapy/diagnostic agents for AD.

Experimental Procedures

Black 384-well low-flange, flat-bottom assay plates were obtained from Corning (New York). Brain lysates of wt and 5XFAD mice were prepared freshly from isolated brains. Thioflavin-T and DMSO were obtained from Sigma Aldrich (St Louis, MO). All other reagents/solvents were of analytical grade, and used as received from commercial source without further purifications.

The 5XFAD mice were maintained at Vanderbilt University under standard conditions, in a 12-h light/dark cycle and with free access to food and water. The 5XFAD mice over express both mutant human APP and PS1 express high APP levels correlating with high burden and accelerated accumulation of the Abeta. A colony of 5XFAD transgenic mice obtained from Jackson Laboratories was maintained by crossing 5XFAD mice with a wild-type (wt) C57BL/6J strain. The mice were genotyped by a standard polymerase chain reaction using DNA isolated from tail tips with the following primers: PSEN1 forward, 5'-TCATGACTATCCTCCTGGTGG-3' (SEQ ID NO: 1) and reverse, 5'-CGTTATAGGTTTTAAACACTTCCCC-3' (SEQ ID NO: 2). For APP, forward, 5'-AGGACTGACCACTCGACCAG-3' (SEQ ID NO: 3) and reverse, 5'-CGGGGGTCTAGTTCTGCAT-3' (SEQ ID NO: 4). The mice were also genotyped for the presence of retinal degeneration Pde6brd1 mutation using forward, 5'-AAGCTAGCTGCAGTAACGCCATTT-3' (SEQ ID NO: 5) and reverse, 5'-ACCTGCATGTGAACCCAGTATTCTATC-3' (SEQ ID NO: 6). After polymerase chain reaction amplification, the DNA product of each reaction was analyzed by size fractionation through a 1% agarose gel; with Pde6b mutant=560 bp, APP transgene=377 bp and PSEN1 transgene=608 bp.

Animal experiments were conducted per the guidelines established by Vanderbilt University's Institutional Animal Care and Use Committee. At the end of the study, animals were euthanized by cervical dislocation after sedated with isoflurane. Clinical signs were used to check after animal euthanasia including heartbeats, toe-pinching for reflection. Further, if animals show signs of illness (weight loss, food withdrawal, or infection) they will be sacrificed before the endpoints. All experimental procedures in this study were approved by the Vanderbilt University IACUC panel.

Brain lysate preparation—Excised midbrains of 5XFAD (8-month-old) or wt mice (age-matched) were homogenized for 5 min in 200 μL of buffer comprised of 21.4 g sucrose, 5 mL of 1 M tris base, and 0.5 mL of 0.5 M EDTA/250 mL DPBS using the T-25 basic Ultra-Turrax homogenizer. Additional 100 μL aliquots of this buffer were then added to the homogenized sample and re-homogenized for 2 min until a total added volume of 800 μL was attained. The sample was diluted to 4 mL total volume using another buffer comprised of 5% BSA, and 0.03% Tween 20 in DPBS solution. Roche Complete protease inhibitor tablets were added to both buffers immediately prior to use (1 tablet/10 mL buffer). The sample was centrifuged at 16,000 g for 30 min at 4° C. Aliquots of the supernatant were stored at −80° C. until use.

HATCO HTS assay—To translate the assay initially performed on a cuvette to a 384-well format, the general protocol includes the following steps: A fresh stock solution of thioflavin-T was prepared in distilled and deionized water after passing through a micro filter. The concentration of total protein was measured according to Beer's law with an extinction coefficient of 26,620 $M^{-1}cm^{-1}$ at 416 nm. The stock solution was stored in darkness using aluminum foil and kept at 4° C. throughout the assay. Unless stated, each assaying well contained 10 μM of thioflavin-T, 5 mg/mL of freshly isolated and homogenized brain lysate (5 μL) obtained from 5XFAD mice and with 30 μM of screening compounds. During the assay development, the positive control was used at a concentration of 100 μM to achieve its maximal effect. For the negative control, the wells contained the same components minus positive control. The protein concentration of brain lysate throughout the study was normalized. After equilibration for 10 min at room temperature, the FL signal of the sample was measured using a Biotek Synergy NEO plate reader at an emission lambda max of 485 nm using an excitation of 465 nm and the signals of the different conditions were analyzed. The final volume per well was 50 μL. All assays were performed using a single dose of screening compounds in triplicate.

Once the preliminary hit compounds were identified, a cross-screening protocol was employed to validate the hits with duplicated concentrations for each hit. Combined with the data in the first run, each candidate has 3 screening values, which enable for statistical analysis. The best fit compounds will be selected for the next screening using 9 concentrations each to determine the tentative $IC_{50}$ values, adapted within the HATCO assay. In this data range, the original test concentration was also included in the analysis. In its finalized 384-well format, this procedure involves 2 phases. In the first phase of the cross-screening procedure, the absorbance profile of each hit compound was evaluated over the 250-900 nm wavelength range in a triplicate fashion using the Synergy Neo Multi-Microplate reader (BioTek). Scatterplots of absorbance as a function of wavelength were then used to qualitatively assess whether the analyzed hit compound significantly absorb at the relevant wavelengths. For example, as the way HATCO assay was designed, a reduction of the emission of thioflavin-T at 485 nm, due to displacement by the small molecule, was the primary indicator of Abeta-binding potential of the small molecule in the assay. If the hit compounds absorbing at this wavelength, they should be considered false positives. To quantitatively cross-screen for false positives secondary to interference of thioflavin-T absorbance or emission at 410 nm and 485 nm, respectively, a separate experimental design was employed. In this second phase of cross-screening, 125 nL of each hit compound (10 mM) was plated with 25 μL of thioflavin-T (10 μM) in triplicate fashion. As a control, 25 μL of 10 μM thioflavin-T was plated in the presence of 125 nL of DMSO. Again, the Synergy Neo Multi-Mode Microplate reader (BioTek) was employed to measure thioflavin-T's emission at 485 nm (excitation 410 nm. Statistical determination of false-positives was accomplished via a Paired 2-tailed Student T-test comparing of the mean fluorescence for the DMSO-treated control wells to that of wells containing thioflavin-T and the positive hit compound. In this work, a P-value <0.05 was used as the threshold statistic for classification as a false positive hit.

Compound library selection—Approximately 3500 compounds selected from NIH Clinical Collection I & II were screened. Many of these small molecules have been used in humans for different purposes. Another library where compounds were selected from is Spectrum collection. This library has a wide range of analogs of biologically active and structurally diverse compounds. Those compounds have known properties and they can be used for prioritization in the screening tier, the compounds including 50% drug components, 30% natural product, and 20% other bioactive components.

All compounds were screened on 11 plates. The Z-prime value was calculated for each plate as a measure of assay quality. Outliers were selected by determining which wells exhibited FL values that fell outside of 3 standard deviations of the means of the FL value of all test compounds on individual plates.

Automatic dispenser and liquid—In a 384-well plate format using fluorescent readout, precise distribution of minutes amount of dye via robotic system as well as participating reagents and solvents is crucial to maintain the quality and reproducibility of the assay. Buffers and solvents were distributed across the plate via the ECHO liquid handling system, while thioflavin-T aliquots and 5XFAD brain lysate were dispensed using the Bravo system. All tip-based dispensers used tip-touch procedure to eliminate the possibility of reagent adhesion to the pipette tips. Each well is thoroughly mixed ten times by the automated liquid handling algorithm to increase equilibrium. To reduce variability between samples secondary to variations in loading, deep-well source plates of thioflavin-T and 5XFAD lysate were generated using the COMBI liquid handling system. It is noteworthy that prior to loading the source plate using the COMBI liquid handling system, all reagents were vortexed for 10 min and sonicated 15 min at 4° C. While the tested compound library was dispensed using the ECHO liquid handling system. The positive control was designed as the observed FL signal in the presence of the promethazine, an Abeta inhibitor that we reported in the past while negative control is associated with the observed FL signal in the absence of promethazine.

Estimation of the assay quality—Before screening a large library of compounds, pilot screens were used to assess the quality of the assay to predict whether the design is suitable for use in a full-scale and high-throughput manner. The Z-prime value incorporates both the dynamic range of the assay as well as well-to-well variability. The Z-prime value is defined in terms of four parameters—the means (μ) and standard deviations (σ) of both the positive (p) and negative (n) controls (μp, σp, and μp, σn), as shown in the formula below:

$$Z\text{-prime} = \frac{3(\sigma_p + \sigma_n)}{|\mu_p - \mu_n|}$$

Where the means (μ) and standard deviations (σ) of both the positive (p) and negative (n) controls (μp, σp, and μn, σn). Z-prime values can be categorized into three groups corresponding to useless, marginal and excellent assays. A hypothetical ideal assay carries a Z-prime value of 1, the maximum Z-prime mathematically possible, whereas a Z-prime value less than 0 indicates that there is too much overlap between positive and negative controls for the assay to be useful. More commonly seen are assays characterized by Z-prime in the range of 0 to 1. In this range, an assay characterized by a Z-prime between 0-0.5 is considered marginally useful while a Z-prime above 0.5 qualifies an assay to be considered excellent.

Example 2

Promethazine Crosses the BBB

HPLC and MALDI-IMS (imaging mass spectrometry) were performed to demonstrate that promethazine crosses the BBB and binds to amyloid-β (Aβ).

Figure 11:
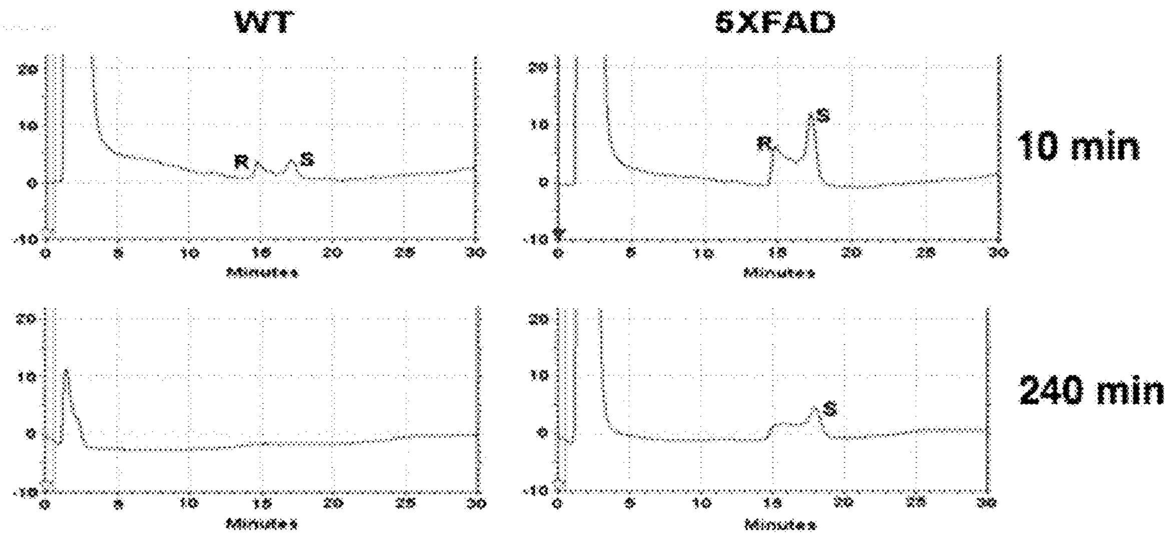
FIG. 11 shows graphs illustrating detectable levels of promethazine in wild-type (WT) and 5XFAD mouse models after injection via the tail vein and subsequent perfusion for 10 minute or 4 hours post-injection.

In the HPLC experiment, WT and 5XFAD mice (n=3, each) were injected with promethazine via the tail veins, and subsequently perfused 10 min or 4 h post-injection. Freshly isolated brains were homogenized to facilitate extraction and quantification via HPLC using the procedure we reported earlier. Ten minutes post-injection, detectable levels of promethazine were measured in both WT (mean=2.57 μg) and 5XFAD (mean=9.62 μg) mouse models, thus confirming promethazine's ability to cross the BBB in both models (FIG. 11).

At this time-point, 0.5% of the original promethazine dose is retained within the brains of WT mice compared to 2% retention in the 5XFAD model. This is approximately a 4-fold increase in promethazine retention in Aβ-burdened brains. At the 240-minute time-point 0.5% of the original dose was retained in 5XFAD brains versus 0.01% in WT mice. Given that the difference in promethazine retention between WT and 5XFAD grows over time, it is believed that the enhanced retention of promethazine in Aβ-burdened brains reflects an affinity of promethazine for Aβ plaques.

Other Phenothiazines Besides Promethazine

The backbone chemical structure of promethazine is phenothiazine. The other phenothiazine analogs discussed herein are intended to cover this family of compounds having a phenothiazine core and/or backbone. Various other phenothiazine analogs include, but are not limited to, those illustrated in FIG. 3.

SAR medicinal chemistry. The synthesis of promethazine analogs begins with phenothiazine ring. If the desired product includes a phenothiazine ring, it can generally be synthesized from an existing phenothiazine ring through a one- or two-step reaction. In contrast, if there are modifications on phenothiazine rings, the ring is synthesized from scratch. The reaction time may be accelerated using the high-throughput microwave synthesizer (Biotage). This device is equipped with an automatic array that enables performance of 30 experiments simultaneously.

Example 3

This Example describes the design and synthesis of positron emission tomography (PET) labeled probes for in vivo molecular imaging. More specifically, this Example focuses on the design and synthesis of a promethazine PET probe 8 for in vivo molecular imaging. Although discussed primarily herein with respect to the promethazine PET probe 8, the concept extends to labeling of the other structurally similar probes, such as phenothiazine analogs, promethazine, and promethazine analogs.

Referring to FIG. 5, the synthesis started first with alkylation reaction using commercial starting material phenothiazine 1 in the presence of NaI and $NaHCO_3$ to afford the desired intermediate 3 with moderate yield. As part of radioisotope labeling, besides making the precursors, such as compound 7, a "cold" compound ("cold" compound is identical to radioisotope-labeled compound, albeit there is no radioisotope attached) was also developed in order to provide physical evidence to support the analytical characterization of the labeled probe. Toward that goal, "cold" compound 5 was synthesized from 3 using dimethyl amine 4 in the presence of sodium triacetoxyborohydride and dimethylacetamide at 50° C. The precursor 7 was achieved using the intermediate 3 with the treatment of methyl amine in the presence of sodium triacetoxyborohydride and dimethylacetamide at room temperature.

For the labeling to obtain the promethazine PET probe 8, the radiochemical synthesis of [$^{11}$C]promethazine is accomplished using the GE Tracerlab FXC-Pro, a commercially supplied reaction platform. Briefly, $^{11}CO_2$ is made by irradiating a target filled with nitrogen and 1% oxygen gas with protons. The $^{11}CO_2$ is then trapped on nickel Shimalite with molecular sieves at room temperature. The $^{11}CO_2$ is then converted to $^{11}CH_4$ by heating the trapped $^{11}CO_2$ to 400° C. in the presence of hydrogen gas. The $^{11}CH_4$ is then released from the nickel Shimalite at 400° C. and isolated on molecular sieves at ~75° C. The $^{11}CH_4$ is then converted to $^{11}CH_3I$ via a recirculation through gaseous iodine at ~720° C., with the $^{11}CH_3I$ being trapped on Porapak N with each cycle. The $^{11}CH_3I$ is then released from the Porapak N by heating with a gentle flow of helium into the reactor which contains a premixed solution of the Promethazine Precursor (1 mg), Sodium Hydride (1.7 mg) in N,N-Dimethylformamide (300 μL). Once all radioactivity has been eluted from the Porapak N, the reaction mixture was heated to 100° C. for 5 min, cooled to room temperature, and diluted with the purification mobile phase (50% Acetonitrile in 100 mM ammonium formate). The reaction mixture was then loaded into the HPLC load loop and injected onto the purification column (Phenomenex C18). The desired radioactive peak is isolated and diluted with water (20 mL) followed by transfer on a C18 Sep-Pak Plus. The Sep-Pak is then washed with water (10 mL) and subsequently eluted with ethanol (1 mL) followed by 0.9% saline (10 mL). This mixture is then passed through a 0.22 μm sterilizing filter and into the final vial. The specific activity is 210 Ci/mmol.

As illustrated in FIGS. 6A-B, the [$^{11}$C]promethazine probes bound to Abeta plaques and were observed via an autoradiography study of human brain tissues collected from patients of Alzheimer's disease. The specificity of the binding can be seen in FIG. 6A, where tissues (10 μm) on glass slides were soaked in [$^{11}$C]promethazine PET probe diluted in PBS solution, when compared to FIG. 6B, which shows tissues were soaked in the same solution as FIG. 6A, albeit with the presence of a large excess of "cold" (unlabeled) promethazine, denoted as PMZ in the figure.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Weuve, J., Hebert, L. E., Scherr, P. A., and Evans, D. A. (2014) Deaths in the United States among persons with Alzheimer's disease (2010-2050). *Alzheimers Dement* 10, e40-46.
2. Philibert, K. D., Marr, R. A., Norstrom, E. M., and Glucksman, M. J. (2014) Identification and characterization of Abeta peptide interactors in Alzheimer's disease by structural approaches. *Front Aging Neurosci* 6, 265.
3. Macias, M. P., Gonzales, A. M., Siniard, A. L., Walker, A. W., Corneveaux, J. J., Huentelman, M. J., Sabbagh, M. N., and Decourt, B. (2014) A cellular model of amyloid precursor protein processing and amyloid-beta peptide production. *J Neurosci Methods* 223, 114-122.
4. Selkoe, D. J. (2011) Alzheimer's disease. *Cold Spring Harb Perspect Biol* 3, 1-16.
5. Weller, R. O., Subash, M., Preston, S. D., Mazanti, I., and Carare, R. O. (2008) Perivascular drainage of amyloid-beta peptides from the brain and its failure in cerebral amyloid angiopathy and Alzheimer's disease. *Brain Pathol* 18, 253-266.
6. Viola, K. L., and Klein, W. L. (2015) Amyloid beta oligomers in Alzheimer's disease pathogenesis, treatment, and diagnosis. *Acta Neuropathol* 129, 183-206.
7. Ryan, T. M., Roberts, B. R., McColl, G., Hare, D. J., Doble, P. A., Li, Q. X., Lind, M., Roberts, A. M., Mertens, H. D., Kirby, N., Pham, C. L., Hinds, M. G., Adlard, P. A., Barnham, K. J., Curtain, C. C., and Masters, C. L. (2015) Stabilization of nontoxic Abeta-oligomers: insights into the mechanism of action of hydroxyquinolines in Alzheimer's disease. *J Neurosci* 35, 2871-2884.
8. Matsuzaki, K. (2014) How do membranes initiate Alzheimer's disease? formation of toxic amyloid fibrils by the amyloid beta-protein ganglioside clusters. *Acc Chem Res* 47, 2397-of 2404.
9. Hong, S., Ostaszewski, B. L., Yang, T., O'Malley, T. T., Jin, M., Yanagisawa, K., Li, S., Bartels, T., and Selkoe, D. J. (2014) Soluble Abeta oligomers are rapidly sequestered from brain ISF in vivo and bind GM1 ganglioside on cellular membranes. *Neuron* 82, 308-319.
10. Collins-Praino, L. E., Francis, Y. I., Griffith, E. Y., Wiegman, A. F., Urbach, J., Lawton, A., Honig, L. S., Cortes, E., Vonsattel, J. P., Canoll, P. D., Goldman, J. E., and Brickman, A. M. (2014) Soluble amyloid beta levels are elevated in the white matter of Alzheimer's patients, independent of cortical plaque severity. *Acta Neuropathol Commun* 2, 83.
11. Chen, J., Armstrong, A. H., Koehler, A. N., and Hecht, M. H. (2010) Small molecule microarrays enable the discovery of compounds that bind the Alzheimer's Abeta peptide and reduce its cytotoxicity. *J Am Chem Soc* 132, 17015-17022.
12. Inglese, J., Shamu, C. E., and Guy, R. K. (2007) Reporting data from high-throughput screening of small-molecule libraries. *Nat Chem Biol* 3, 438-441.
13. Nolting, D. D., Gore, J. C., and Pham, W. (2011) NEAR-INFRARED DYES: Probe Development and Applications in Optical Molecular Imaging. *Annual review of cell and developmental biology* 8, 521-534.
14. Nesterov, E. E., Skoch, J., Hyman, B. T., Klunk, W. E., Bacskai, B. J., and Swager, T. M. (2005) In vivo optical imaging of amyloid aggregates in brain: design of fluorescent markers. *Angewandte Chemie* (*International ed* 44, 5452-5456.
15. Hudson, S. A., Ecroyd, H., Kee, T. W., and Carver, J. A. (2009) The thioflavin T fluorescence assay for amyloid fibril detection can be biased by the presence of exogenous compounds. *FEBS J* 276, 5960-5972.
16. Khurana, R., Coleman, C., Ionescu-Zanetti, C., Carter, S. A., Krishna, V., Grover, R. K., Roy, R., and Singh, S. (2005) Mechanism of thioflavin T binding to amyloid fibrils. *J Struct Biol* 151, 229-238.
17. LeVine III, H. (1993) Thioflavine T interaction with synthetic Alzheimer's diease beta-amyloid peptides: detection of amyloid aggregation in solution. *Protein Sci* 2, 404-410.
18. Naiki, H., Higuchi, K., Hosokawa, M., and Takeda, T. (1989) Fluorometric determination of amyloid fibrils in vitro using the fluorescent dye, thioflavin T1. *Anal Biochem* 177, 244-249.
19. Klunk, W. E., Jacob, R. F., and Mason, R. P. (1999) Quantifying amyloid by congo red spectral shift assay. *Methods Enzymol* 309, 285-305.
20. Klunk, W. E., Jacob, R. F., and Mason, R. P. (1999) Quantifying amyloid beta-peptide (Abeta) aggregation using the Congo red-Abeta (CR-abeta) spectrophotometric assay. *Anal Biochem* 266, 66-76.
21. Nakagami, Y., Nishimura, S., Murasugi, T., Kubo, T., Kaneko, I., Meguro, M., Marumoto, S., Kogen, H., Koyama, K., and Oda, T. (2002) A novel compound RS-0466 reverses beta-amyloid-induced cytotoxicity through the Akt signaling pathway in vitro. *Eur J Pharmacol* 457, 11-17.
22. Nishimura, S., Murasugi, T., Kubo, T., Kaneko, I., Meguro, M., Marumoto, S., Kogen, H., Koyama, K., Oda, T., and Nakagami, Y. (2003) RS-4252 inhibits amyloid beta-induced cytotoxicity in HeLa cells. *Pharmacol Toxicol* 93, 29-32.
23. Wood, S. J., MacKenzie, L., Maleeff, B., Hurle, M. R., and Wetzel, R. (1996) Selective inhibition of Abeta fibril formation. *J Biol Chem* 271, 4086-4092.
24. Manzoni, C., Colombo, L., Messa, M., Cagnotto, A., Cantu, L., Del Favero, E., and Salmona, M. (2009) Overcoming synthetic Abeta peptide aging: a new approach to an age-old problem. *Amyloid* 16, 71-80.
25. Oakley, H., Cole, S. L., Logan, S., Maus, E., Shao, P., Craft, J., Guillozet-Bongaarts, A., Ohno, M., Disterhoft, J., Van Eldik, L., Berry, R., and Vassar, R. (2006) Intraneuronal beta-amyloid aggregates, neurodegeneration, and neuron loss in transgenic mice with five familial Alzheimer's disease mutations: potential factors in amyloid plaque formation. *J Neurosci* 26, 10129-10140.

26. Selkoe, D. J., and Hardy, J. (2016) The amyloid hypothesis of Alzheimer's disease at 25 years. *EMBO Mol Med* 8, 595-608.
27. Parikh, N. D., and Klimov, D. K. (2015) Molecular Mechanisms of Alzheimer's Biomarker FDDNP Binding to Abeta Amyloid Fibril. *J Phys Chem B* 119, 11568-11580.
28. He, H., Xu, J., Cheng, D. Y., Fu, L., Ge, Y. S., Jiang, F. L., and Liu, Y. (2017) Identification of Binding Modes for Amino Naphthalene 2-Cyanoacrylate (ANCA) Probes to Amyloid Fibrils from Molecular Dynamics Simulations. *J Phys Chem B* 121, 1211-1221.
29. Klunk, W. E., Wang, Y., Huang, G. F., Debnath, M. L., Holt, D. P., Shao, L., Hamilton, R. L., Ikonomovic, M. D., DeKosky, S. T., and Mathis, C. A. (2003) The binding of 2-(4'-methylaminophenyl)benzothiazole to postmortem brain homogenates is dominated by the amyloid component. *J Neurosci* 23, 2086-2092.
30. Doig, A. J., Del Castillo-Frias, M. P., Berthoumieu, O., Tarus, B., Nasica-Labouze, J., Sterpone, F., Nguyen, P. H., Hooper, N. M., Faller, P., and Derreumaux, P. (2017) Why Is Research on Amyloid-beta Failing to Give New Drugs for Alzheimer's Disease? *ACS Chem Neurosci* 8, 1435-1437.
31. Jerabek, J., Uliassi, E., Guidotti, L., Korabecny, J., Soukup, O., Sepsova, V., Hrabinova, M., Kuca, K., Bartolini, M., Pena-Altamira, L. E., Petralla, S., Monti, B., Roberti, M., and Bolognesi, M. L. (2017) Tacrine-resveratrol fused hybrids as multi-target-directed ligands against Alzheimer's disease. *Eur J Med Chem* 127, 250-262.
32. Loureiro, J. A., Andrade, S., Duarte, A., Neves, A. R., Queiroz, J. F., Nunes, C., Sevin, E., Fenart, L., Gosselet, F., Coelho, M. A., and Pereira, M. C. (2017) Resveratrol and Grape Extract-loaded Solid Lipid Nanoparticles for the Treatment of Alzheimer's Disease. *Molecules* 22.
33. Moussa, C., Hebron, M., Huang, X., Ahn, J., Rissman, R. A., Aisen, P. S., and Turner, R. S. (2017) Resveratrol regulates neuro-inflammation and induces adaptive immunity in Alzheimer's disease. *J Neuroinflammation* 14, 1.
34. Sarubbo, F., Moranta, D., Asensio, V. J., Miralles, A., and Esteban, S. (2017) Effects of Resveratrol and other Polyphenols on the most common Brain Age-Related Diseases. *Curr Med Chem.*
35. McClure, R. A., Chumbley, C. W., Reyzer, M. L., Wilson, K., Caprioli, R. M., Gore, J. C., and Pham, W. (2013) Identification of promethazine as an amyloid-binding molecule using a fluorescence high-throughput assay and MALDI imaging mass spectrometry. *NeuroImage: Clinical* 2, 620-629.
36. Day, L. R., gibson, W., and Williams, K. P. (2010) Development of a high throughput screening assay for inhibitors of hedgehog-heparin interactions. *int J High Throughput Screening* 1, 69-80.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. An amyloid-binding compound comprising a phenothiazine core;

an acyclic nitrogen atom that is not directly attached to the phenothiazine core; and a positron emission tomography (PET) radioisotope label selected from [$^{11}$C]carbon, or [$^{18}$F]fluoride;

wherein the radioisotope label is attached to said acyclic nitrogen atom.

2. The compound of claim 1, wherein the ring nitrogen at position 10 of the phenothiazine core is attached to an N,N-dimethylpropan-2-amine moiety.

3. A compound selected from:

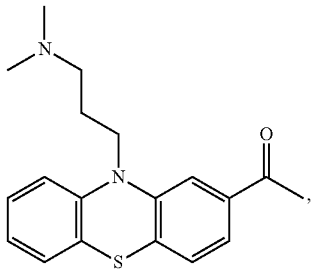
,

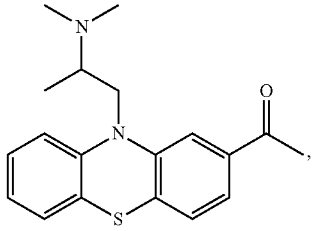
,

-continued

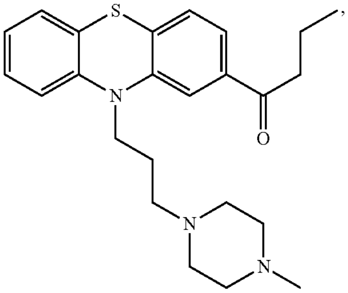
,

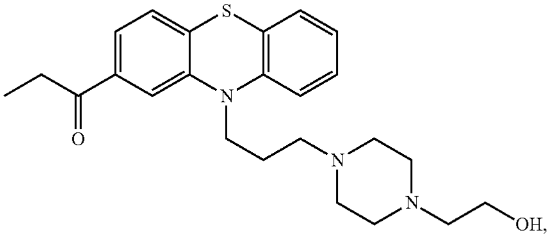
,

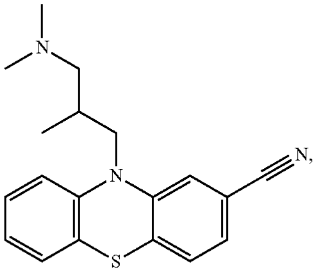
,

-continued
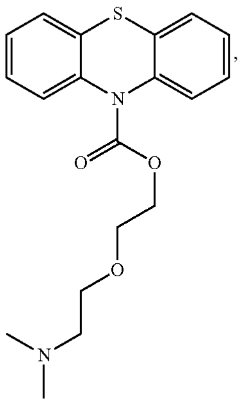,
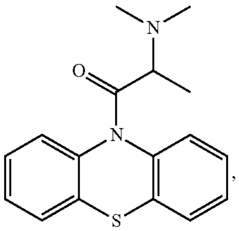,
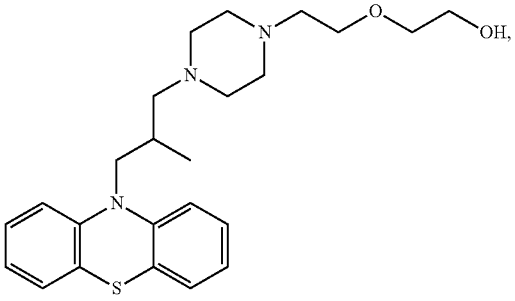
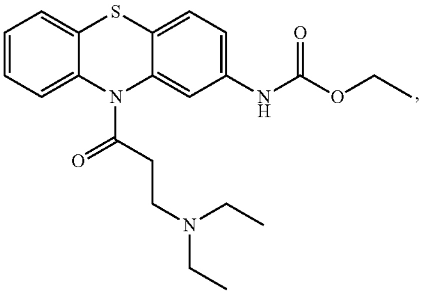,
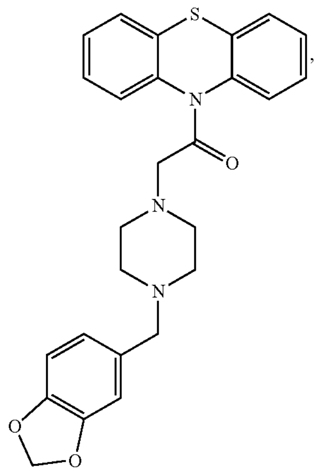,
-continued
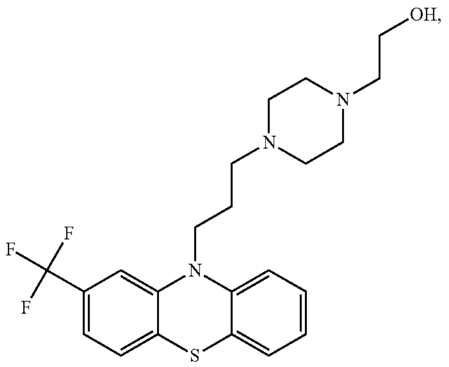
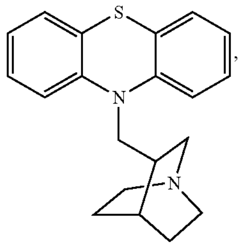,
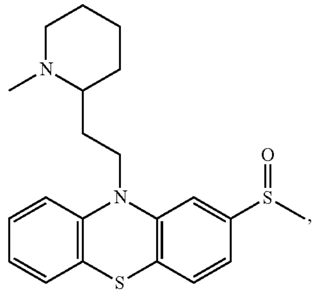,
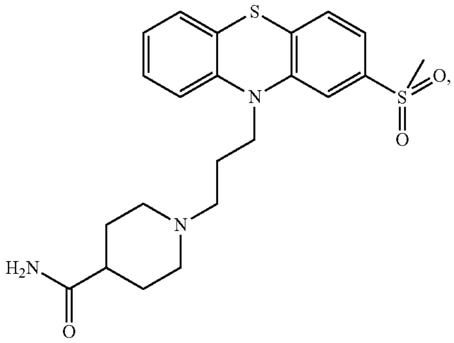
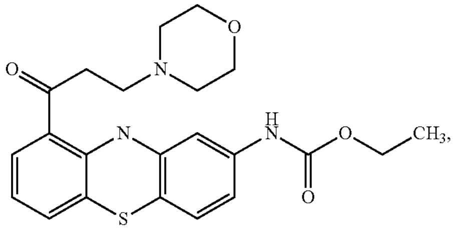
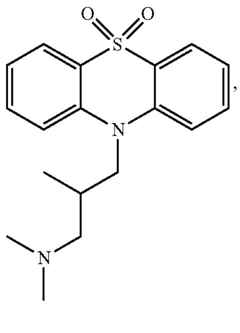,
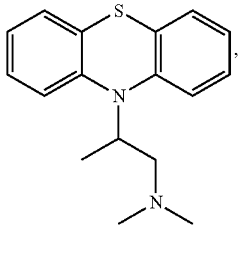, -continued

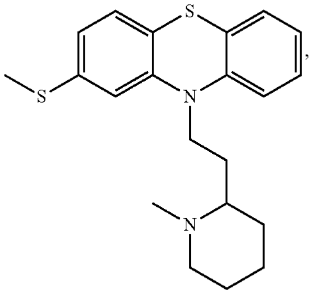
,

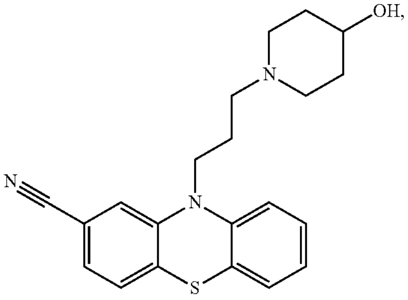
,

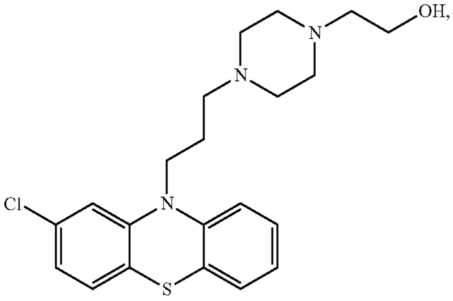
,

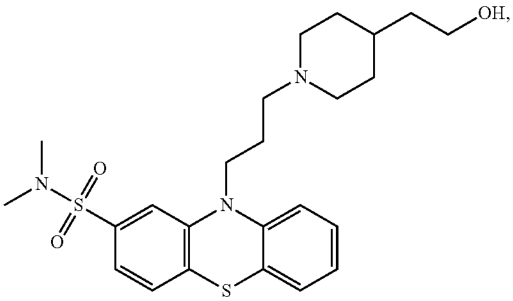
,

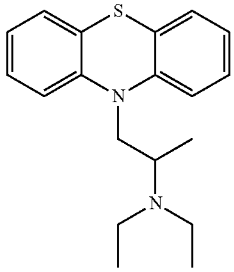
, and

-continued

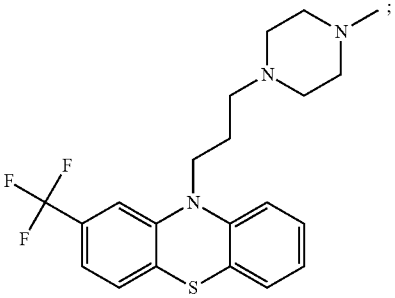
;

wherein the compound further comprises a positron emission tomography (PET) radioisotope label attached to a nitrogen atom that is not part of the phenothiazine core.

4. The compound of claim 1, wherein the radioisotope is [$^{11}$C]carbon.

5. A method of detecting amyloid-β (Abeta) plaques in a subject, the method comprising:

administering one or more of the compounds of claim 1 to the subject; and detecting the compound within the subject through autoradiography.

6. A compound of claim 1, wherein the amyloid-binding compound is selected from:

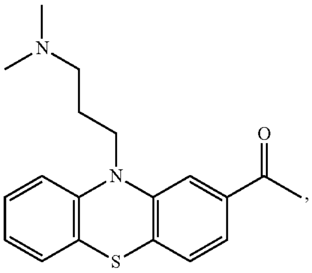
,

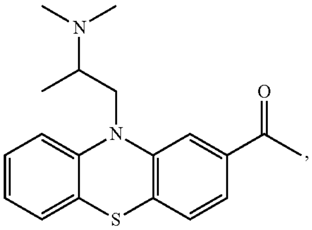
,

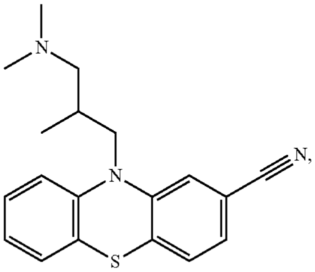
,

-continued
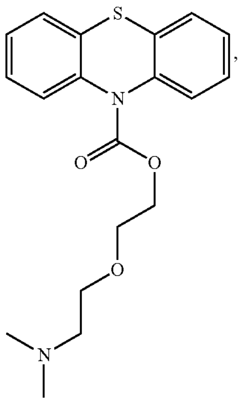
,
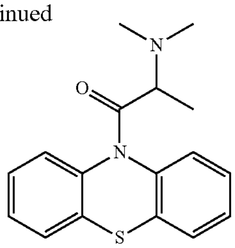
,
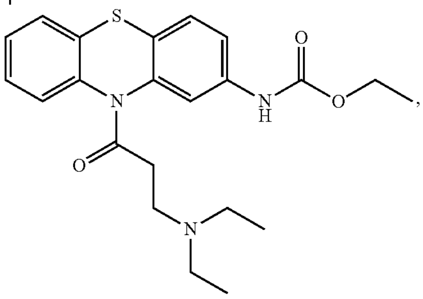
,
-continued
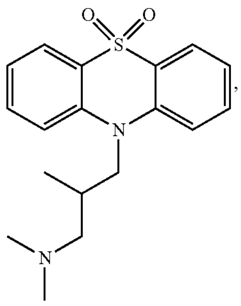
,
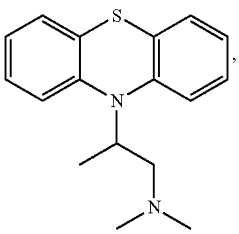
, and
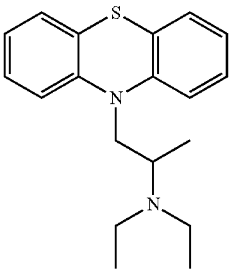
.
* * * * *

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial
<220> FEATURE:
<223> OTHER INFORMATION: PSEN1 Forward Primer

<400> SEQUENCE: 1

tcatgactat cctcctggtg g                                               21


<210> SEQ ID NO 2
<211> LENGTH: 25
<212> TYPE: DNA
<213> ORGANISM: Artificial
<220> FEATURE:
<223> OTHER INFORMATION: PSEN1 Reverse Primer

<400> SEQUENCE: 2

cgttataggt tttaaacact tcccc                                           25


<210> SEQ ID NO 3
<211> LENGTH: 20
<212> TYPE: DNA
<213> ORGANISM: Artificial
<220> FEATURE:
<223> OTHER INFORMATION: APP Forward Primer

<400> SEQUENCE: 3

aggactgacc actcgaccag                                                 20
```

-continued

<210> SEQ ID NO 4
<211> LENGTH: 19
<212> TYPE: DNA
<213> ORGANISM: Artificial
<220> FEATURE:
<223> OTHER INFORMATION: APP Reverse Primer

<400> SEQUENCE: 4
cgggggtcta gttctgcat 19

<210> SEQ ID NO 5
<211> LENGTH: 24
<212> TYPE: DNA
<213> ORGANISM: Artificial
<220> FEATURE:
<223> OTHER INFORMATION: Pde6brd1 Mutation Forward Primer

<400> SEQUENCE: 5
aagctagctg cagtaacgcc attt 24

<210> SEQ ID NO 6
<211> LENGTH: 27
<212> TYPE: DNA
<213> ORGANISM: Artificial
<220> FEATURE:
<223> OTHER INFORMATION: Pde6brd1 Mutation Reverse Primer

<400> SEQUENCE: 6
acctgcatgt gaacccagta ttctatc 27